United States Patent [19]
Rabin et al.

[11] Patent Number: 5,795,721
[45] Date of Patent: Aug. 18, 1998

[54] HIGH AFFINITY NUCLEIC ACID LIGANDS OF ICP4

[75] Inventors: Ross S. Rabin; Sumedha D. Jayasena; Larry Gold. all of Boulder, Colo.

[73] Assignee: NeXstar Pharmaceuticals, Inc., Boulder, Colo.

[21] Appl. No.: 591,989

[22] Filed: Jan. 25, 1996

Related U.S. Application Data

[63] Continuation-in-part of Ser. No. 409,442, Mar. 24, 1995, Pat. No. 5,696,249, which is a continuation of Ser. No. 714,131, Jun. 10, 1991, Pat. No. 5,475,096, which is a continuation-in-part of Ser. No. 536,428, Jun. 11, 1990, abandoned.

[51] Int. Cl.$^6$ ............... C12Q 1/68; C12P 19/34; G01N 33/566; C07H 21/02

[52] U.S. Cl. ............... 435/6; 435/91.1; 435/91.2; 436/501; 536/23.1

[58] Field of Search ............... 435/91.2, 6, 91.1; 536/23.1; 436/501

[56] References Cited

U.S. PATENT DOCUMENTS 5,475,096  12/1995  Gold et al. ............... 536/23.1

FOREIGN PATENT DOCUMENTS

| 2 183 661 A | 6/1987 | United Kingdom . |
| WO/89/06694 | 7/1989 | WIPO . |
| 92/14843 | 9/1992 | WIPO . |

OTHER PUBLICATIONS

Faber et al. Association of the herpes simplex virus regulatory protein ICP4 with specific nucleotide sequence in DNA. Nucleic Acids Research, vol. 14 (15), pp. 6067–6083, 1986.
Cantin et al. (1992) Adv. Exp. Med. Biol. 312:319.
Clusel et al. (1995) Gene Expression 4:301.
Crooke et al. (1992) Antimicrobial Agents and Chemotherapy 36:527.
Draper et al. (1990) Antiviral Research 13:151.
Ellington and Szostak (1990) Abstract of papers presented at the 1990 meeting on RNA Processing, Cold Spring Harbor Laboratory, Cold Spring Harbor, NY, p. 226.
Fennewald et al. (1995) Antiviral Research 26:37.
Gao et al. (1990) Antimicrobial Agents and Chemotherapy 34:808.
Gao et al. (1990) J. Biol. Chem. 265:20172.
Hoke et al. (1991) Nucleic Acids Research 216:19.
Jacob et al. (1993) Eur. J. Biochem. 216:19.
Joyce (1989) Gene 82:83.
Joyce and Inoue (1989) Nucleic Acids Research 17:711.
Kinzler and Vogelstein (1989) Nucleic Acids Research 17:3645.
Kmetz et al. (1991) Antiviral Research 16:173.
Kramer et al. (1974) J. Mol. Biol. 89:719.
Kulka et al. (1993) Antiviral Research 20:115.
Kulka et al. (1994) Antimicrobial Agents and Chemotherapy 38:675.
Kulka et al. (1989) Proc. Natl. Acad. Sci. USA 86:6868.
Levisohn and Speigelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Orgel (1979) Proc. R. Soc. Lond. B205:435.
Peyman et al. (1995) Biol. Chem. Hoppe–Seyler 376:195.
Poddevin et al. (1994) Antisense Research and Development 4:147.
Robertson and Joyce (1990) Nature 344:467.
Smith et al. (1986) Proc. Natl. Acad. Sci. USA 83:2787.
Thiesen and Bach (1990) Nucleic Acids Research 18:3203.
Vinogradov et al. (1994) Biochemical and Biophysical Research Communications 203:959.
Whitton (1994) Advances in Virus Research 44:267.

Primary Examiner—Stephanie W. Zitomer
Assistant Examiner—Joyce Tung
Attorney, Agent, or Firm—Swanson & Bratschun LLC

[57] ABSTRACT

Methods are described for the identification and preparation of high-affinity nucleic acid ligands to Transcripion Regulatory Factors, specifically ICP4. Included in the invention are specific ssDNA and RNA ligands to ICP4 identified by the SELEX method.

13 Claims, No Drawings

HIGH AFFINITY NUCLEIC ACID LIGANDS OF ICP4

This application is a Continuation-in-Part of U.S. patent application Ser. No. 08/409,442, filed Mar. 24, 1995, now U.S. Pat. No. 5,696,249 entitled "Nucleic Acid Ligands", which is a Continuation of U.S. patent application Ser. No. 07/714,131, filed Jun. 10, 1991, entitled "Nucleic Acid Ligands", now issued as U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment", now abandoned.

FIELD OF THE INVENTION

Described herein are methods for identifying and preparing high-affinity Nucleic Acid Ligands to transcription regulatory factors, specifically ICP4. The method utilized herein for identifying such Nucleic Acid Ligands is called SELEX, an acronym for Systematic Evolution of Ligands by EXponential enrichment. This invention includes high affinity Nucleic Acid Ligands of transcription regulatory factors, and specific Nucleic Acid Ligands of ICP4. Further disclosed are ssDNA ligands to ICP4. Also disclosed are RNA ligands of ICP4. The oligonucleotides of the present invention are useful as pharmaceuticals or diagnostic agents.

BACKGROUND OF THE INVENTION

Herpes simplex virus infection

Herpes simplex virus types 1 and 2 (HSV-1 and HSV-2) are the etiological agents of several clinically-significant conditions including oropharyngeal infections, skin infections, ocular infection, and central nervous system disorders such as meningitis and encephalitis (reviewed in reference 42). HSV-1 and HSV-2 seropositive individuals are found in virtually all human populations. In the United States, it is estimated that greater than 60% and 16% of the population is seropositive for HSV-1 and HSV-2, respectively.

Primary HSV infection is often asymptomatic. However, HSV infection, whether or not it is asymptomatic, invariably leads to establishment of latent viral infection in nerve cells. No known treatment is available for latent infection, which is a persistent condition. The consequences of latent infection for the individual cover a spectrum from no symptoms for an entire lifetime, to repeated and/or severe episodes of viral disease.

Due to the many HSV-seropositive individuals who are asymptomatic, the number of people who suffer from HSV-related conditions is less than the number of carriers. This means that clinical surveys underestimate the incidence of HSV infection (reviewed in reference 42). For example, HSV-1-mediated oral herpes occurs in 15–45% of adults in Western countries; this number represents between 40–70% of those who carry HSV-1. HSV-2-mediated genital herpes afflicts a minority of those infected, so that the number of HSV-2 sufferers is generally between 1 and 5% of the general population in the U.S. Since HSV-2 is primarily spread by sexual contact, the incidence of infection varies considerably among different demographic groups who differ in their sexual behavior.

Most HSV-related disorders are not life-threatening, although they do represent a significant proportion of doctor visits for sexually transmitted diseases. Affected individuals often seek ameliorative treatment to counteract the discomfort caused by HSV lesions. By contrast, the more serious and potentially life-threatening HSV-related CNS disorders occur infrequently in adults and children. Among neonates, however, HSV infection is almost always symptomatic, and over 50% are afflicted by CNS disorders (65). Without appropriate antiviral treatment, CNS infection in neonates leads to greater than 60% mortality. Estimates of neonatal herpes infection are between 1 in 3,500 and 1 in 5,000 live births (65). Two-thirds of neonatal herpes cases are caused by HSV-2. Due to the increasing percentage of HSV-2-infected pregnant women (20% in the U.S.), neonatal herpes presents a serious public health problem (64).

Molecular biology of HSV

The HSV genome is a double-stranded closed circular DNA molecule consisting of $1.5 \times 10^5$ base pairs, encoding more than 75 polypeptides (reviewed in reference 50). The infective HSV life cycle is governed by three stages of gene expression referred to as immediate-early (IE), middle, and late (also referred to as a, b, and g). Each of these stages results in expression of genes whose products are required for subsequent events in the HSV life cycle, culminating in production and release of infective HSV virions.

Following entry of the HSV virion into the cell, its protein coat is shed, releasing a capsid structure which transports the viral genome to the nuclear pores and into the nucleus. This marks the beginning of the immediate-early stage. Five IE genes are immediately expressed. At least three of these proteins, ICP0, ICP4, and ICP27, are factors involved in regulation of HSV gene expression (ICP, infected-cell polypeptide). These regulatory factors are expressed throughout the life cycle, and they serve to control the complex patterns of gene activation, repression, and de-repression which determine the course of HSV proliferation. Middle genes primarily encode proteins involved in DNA replication, and late genes encode structural proteins involved in packaging and assembling mature virions.

ICP4 protein in HSV-1 and HSV-2

The ICP4 protein (also known as IE175 and Vmw175) is the major transcriptional regulator of HSV gene expression (reviewed in reference 50). The ICP4 gene (also known as the a4 gene) encodes a polypeptide of 1298 amino acids with a predicted molecular weight of 133,000-daltons The mature ICP4 protein exists as a homodimer of 350,000-daltons; the large molecular weight reflects post-translational modifications. The ICP4 homodimer is a double-stranded DNA binding protein which functions both as a transcriptional repressor and activator of HSV gene expression (2, 16, 17, 20, 26, 27, 29, 34, 47, 48, 59). The actual mechanisms by which it affects transcription are not well understood. The most well-characterized DNA binding sites are those where ICP4 acts as a repressor. Computer analysis of known ICP4 repression sites has led to a definition of a loose consensus binding site: RTCGTCNNYNYSG (SEQ ID NO:1), where R=A or G, N=any base, Y=C or T, and S=C or G (reviewed in reference 11).

ICP4 is an essential gene product whose function is required for HSV proliferation (10). HSV-1 mutants which lack both copies of the ICP4 gene (there are two in different loci in the genome) fail to replicate DNA and produce new virions (10). In addition to ICP4, other essential proteins are glycoproteins B and D (gB and gD), ICP27, and several proteins involved in DNA replication (reviewed in references 38, 41, 50). As mentioned above, the action of ICP4 is required throughout the HSV life cycle because of its essential role in viral gene expression.

ICP4 is a modular protein comprised of five regions (39). Extensive biochemical and genetic analysis has determined the protein domains involved in DNA binding, dimerization, and trans-activation (8–10, 18, 19, 43, 44, 52–56, 61, 62, 68). These studies demonstrate the modularity of the ICP4 protein, based on functional dissection utilizing truncated proteins, altered function mutants, and genetic complementation. Interestingly, the DNA-binding and dimerization functions co-localize to a single domain found in the N-terminal half of the protein (see Table 1).

The biochemical and molecular genetic literature on ICP4 has mostly focused on HSV-1. In general, HSV-1 molecular biology has received much more attention than that of HSV-2, but it is generally agreed that the two viruses perform most critical functions in the same manner, with very closely related proteins. Not surprisingly, the ICP4 proteins from HSV-1 and HSV-2 are functionally interchangeable, based on genetic recombination experiments between the two viruses (58). These experiments demonstrated that virtually any region of the two genes can be interchanged with no alteration in function. Consistent with these data is the fact that HSV-1 and -2 have nearly identical ICP4 amino acid sequences based on analysis of their respective gene sequences (40).

ICP4 homologs in other herpesviruses

HSV-1 and -2 belong to the human herpesviruses which also includes varicella-zoster virus (VZV). HSV-1, HSV-2, and VZV are classified as alpha-herpesviruses in a group with several animal viruses, including pseudorabies virus (PRV), an important pathogen of domesticated swine. ICP4 homologs have been identified in several herpesviruses, including VZV and PRV, in which the proteins are called gp62 and IE180, respectively. Among the ICP4 homologs, the two regions of highest similarity are the DNA-binding/dimerization domain and the transactivation domain.

A sequence alignment of the DNA-binding/dimerization domains of ICP4 from HSV-1 (39), VZV (7), and PRV (4) reveals a high degree of amino acid identity between the three proteins (Table 1; SEQ ID NOS:2–4). Critical to the DNA-binding function are the conserved residues WLQN (residues 490–493 in HSV ICP4), which are probably directly involved in contact with DNA (60). The ICP4 homologs from HSV-1 and VZV are at least partially interchangeable in function, based on both in vitro and in vivo functional assays (12, 13, 21). In addition, a monoclonal antibody raised against the DNA-binding domain of HSV-1 ICP4 cross-reacts with the equivalent domain of the VZV 140 k protein (15).

Therapeutic approaches.

Anti-HSV drugs disrupt HSV proliferation and thereby reduce the severity of viral infection. Existing treatments for HSV have been recently reviewed (1). Two major problems with existing HSV treatments reveal the need for novel therapeutic approaches. 1) Acyclovir, the preeminent antiviral, is an effective systemic drug, but is fairly ineffective in topical applications (1). 2) Viral resistance to acyclovir and other anti-viral agents is increasingly problematic in the clinic, particularly among immuno-compromised patients (23).

Other oligonucleotide-based approaches to HSV inhibition

Many published research studies describe experiments which use antisense technology to target specific DNA or mRNA sequences involved in the HSV life cycle (3, 6, 14, 28, 30, 33, 35–37, 46, 49, 57, 63, reviewed in reference 66).

In another set of studies, non-sequence-specific oligonucleotides apparently interfere with HSV proliferation by an unknown mechanism, perhaps related to preventing HSV adsorption to the cell surface (22, 24, 25).

A recent study describes hairpin oligonucleotides containing ICP4 recognition sequences which bind to the ICP4 protein (5). Clusel et al. term their hairpin molecules "decoy phosphodiester oligonucleotides," which bind ICP4 in vitro, and inhibit HSV-1 proliferation in Vero cells in culture. Clusel and colleagues used a rational approach to design their oligonucleotides based on knowledge of known dsDNA ICP4 binding sites.

SELEX

A method for the in vitro evolution of Nucleic Acid molecules with highly specific binding to Target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, and U.S. patent application Ser. No. 07/931,473, filed Aug. 17, 1992, entitled "Nucleic Acid Ligands," now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a Nucleic Acid Ligand to any desired Target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the Target under conditions favorable for binding, partitioning unbound Nucleic Acids from those Nucleic Acids which have bound specifically to Target molecules, dissociating the Nucleic Acid-Target complexes, amplifying the Nucleic Acids dissociated from the Nucleic Acid-Target complexes to yield a ligand-enriched mixture of Nucleic Acids, then reiterating the steps of binding, partitioning, dissociating and amplifying through as many cycles as desired to yield highly specific, high affinity Nucleic Acid Ligands to the Target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting Nucleic Acid Ligands containing photoreactive groups capable of binding and/or photocrosslinking to and/or photoinactivating a Target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now issued as U.S. Pat. No. 5,567,588, describes a SELEX-based method which achieves highly efficient partitioning between oligonucleotides having high and low affinity for a Target molecule. U.S. patent application Ser. No. 07/964,624, filed Oct. 21, 1992, entitled "Methods of Producing Nucleic Acid Ligands" now issued as U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its Target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleotides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" now issued as U.S. Pat. No. 5,637,459, and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing Nucleic Acid Ligands to transcription regulatory factors. Specifically included are methods of identifying and producing Nucleic Acid Ligands to ICP4 and members of the ICP4 protein family and proteins that are substantially homologous thereto, or analogous transcription factors from other herpesviruses, specifically gp62 and IE180, and the Nucleic Acid Ligands so identified and produced. By substantially homologous it is meant a degree of amino acid sequence identity of 80% or more. Nucleic acid ligand sequences are provided that are capable of binding specifically to ICP4. In particular, ssDNA sequences are provided that are capable of binding specifically the ICP4. Specifically included in the invention are the ssDNA ligand sequences shown in Table 5 and 7–8 (SEQ ID NOS: 17–57, 59–74). Also included are RNA sequences that are capable of binding specifically to ICP4. Specifically included in the invention are the RNA ligand sequences shown in Table 9 (SEQ ID NOS: 75–86). Also included in the invention are ssDNA and RNA ligands that inhibit the function of ICP4.

Further included in this invention is a method of identifying Nucleic Acid Ligands and Nucleic Acid Ligand sequences to transcription regulatory factors comprising the steps of (a) preparing a Candidate Mixture of Nucleic Acids, (b) contacting the Candidate Mixture of Nucleic Acids with a transcription regulatory factor, (c) partitioning between members of said Candidate Mixture on the basis of affinity to the transcription regulatory factor, and (d) amplifying the selected molecules to yield a mixture of Nucleic Acids enriched for Nucleic Acid sequences with a relatively higher affinity for binding to the transcription regulatory factor.

More specifically, the present invention includes the ssDNA ligands to ICP4, identified according to the above-described method, including those ligands shown in Tables 5 and 7–8 (SEQ ID NOS:17–57, 59–74). Also included in the present invention are RNA ligands to ICP4 identified according to the above-described method, including those ligands shown in Table 9 (SEQ ID NOS:75–86). Also included are DNA and RNA ligands to ICP4 that are substantially homologous to any of the given ligands and that have substantially the same ability to bind ICP4 and inhibit the function of ICP4. Further included in this invention are Nucleic Acid Ligands to ICP4 that have substantially the same structural form as the ligands presented herein and that have substantially the same ability to bind said ICP4 and inhibit the function of said ICP4

The present invention also includes modified nucleotide sequences based on the ssDNA and RNA ligands identified herein and mixtures of the same.

DETAILED DESCRIPTION OF THE INVENTION

DEFINITIONS:

"Nucleic Acid Ligand" as used herein is a non-naturally occurring Nucleic Acid having a desirable action on a Target. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule. Nucleic Acid Ligands include Nucleic Acids that are identified from a Candidate Mixture of Nucleic Acids, said Nucleic Acid Ligand being a ligand of a given Target by the method comprising: a) contacting the Candidate Mixture with the Target, wherein Nucleic Acids having an increased affinity to the Target relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. In the present invention, the SELEX methodology is employed to obtain Nucleic Acid Ligands to transcription regulatory factors.

The SELEX methodology is described in the SELEX Patent Applications.

"SELEX Target" or "Target" means any compound or molecule of interest for which a ligand is desired. A Target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX Targets are protein transcription regulatory factors.

"Transcription Regulatory Factors" means viral regulatory factors that are proteinaceous factors that are involved in transcription regulation. Examples of transcriptional regulatory factors are the proteins ICPO, ICP4 and ICP27 from herpes simplex virus type 1.

"ICP4 protein family" means viral regulatory proteins which have amino acid sequences homologous to that of ICP4 from herpes simplex virus type 1. Based on phylogenetic comparisons of currently known sequences, a family (ICP4 protein family) has been defined and has protein members in the following viruses: herpes simplex virus types 1 and 2, equine herpesvirus, pseudorabies virus, varicella zoster virus, and Marek's disease virus (40). This list does not preclude the possibility that additional ICP4 homologs will be described in other viruses.

SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-Target pairs between the Target and those Nucleic Acids having the strongest affinity for the Target.

3) The Nucleic Acids with the highest affinity for the Target are partitioned from those Nucleic Acids with lesser affinity to the Target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity to the Target are then amplified to create a new Candidate Mixture that is enriched in Nucleic Acids having a relatively higher affinity for the Target.

5) By repeating the partitioning and amplifying steps above, the newly formed Candidate Mixture contains fewer and fewer weakly binding sequences, and the average degree of affinity of the Nucleic Acids to the Target will generally increase. Taken to its extreme, the SELEX process will yield a Candidate Mixture containing one or a small number of unique Nucleic Acids representing those Nucleic Acids from the original Candidate Mixture having the highest affinity to the Target molecule.

The SELEX Patent Applications describe and elaborate on this process in great detail. Included are Targets that can be used in the process; methods for partitioning Nucleic Acids within a Candidate Mixture; and methods for amplifying partitioned Nucleic Acids to generate enriched Candidate Mixture. The SELEX Patent Applications also describe ligands obtained to a number of target species, including both protein Targets where the protein is and is not a Nucleic Acid binding protein.

The Nucleic Acid Ligands to Transcription Regulatory Factors can be complexed with a lipophilic compound (e.g., cholesterol) or attached to or encapsulated in a complex comprised of lipophilic components (e.g., a liposome). U.S. patent application Ser. No. 08/434,465, filed May 4, 1995, entitled "Nucleic Acid Ligand Complexes," which is incorporated in its entirety herein, describes a method for preparing a therapeutic or diagnostic complex comprised of a Nucleic Acid Ligand and a lipophilic compound or a non-immunogenic, high molecular weight compound.

The methods described herein and the Nucleic Acid Ligands identified by such methods are useful for both therapeutic and diagnostic purposes. Therapeutic uses include the treatment or prevention of diseases or medical conditions in human patients, specifically diseases caused by herpes viruses. In the preferred embodiment of the present invention, the disease is caused by herpesvirus type 1 or 2. Diagnostic utilization may include both in vivo or in vitro diagnostic applications. The SELEX method generally, and the specific adaptations of the SELEX method taught and claimed herein specifically, are particularly suited for diagnostic applications. SELEX identifies Nucleic Acid Ligands that are able to bind targets with high affinity and with surprising specificity. These characteristics are, of course, the desired properties one skilled in the art would seek in a diagnostic ligand.

The Nucleic Acid Ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any Nucleic Acid Ligand by procedures known in the art to incorporate a labeling tag in order to track the presence of such ligand. Such a tag could be used in a number of diagnostic procedures. The Nucleic Acid Ligands to ICP4 described herein may specifically be used for identification of the ICP4 protein.

SELEX provides high affinity ligands of a target molecule. This represents a singular achievement that is unprecedented in the field of Nucleic Acids research. The present invention applies the SELEX procedure to the specific target of ICP4, a transcriptional regulator of HSV gene expression. In the Example section below, the experimental parameters used to isolate and identify the Nucleic Acid Ligands to ICP4 are described.

In order to produce Nucleic Acids desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand have the highest possible affinity to the target.

In co-pending and commonly assigned U.S. patent application Ser. No. 07/964,624, filed Oct. 21, 1992 ('624), now issued as U.S. Pat. No. 5,496,938, methods are described for obtaining improved Nucleic Acid Ligands after SELEX has been performed. The '624 application, entitled Methods of Producing Nucleic Acid Ligands, is specifically incorporated herein by reference.

In the present invention, two SELEX experiments were performed in order to identify ssDNA and RNA with specific high affinity for ICP4 from degenerate libraries containing 40 random positions (40N) (Example 1). This invention includes the specific ssDNA and RNA ligands to ICP4 shown in Tables 5 and 7–9 (SEQ ID NOS: 17–57, 59–86), identified by the method described in Example 1. This invention further includes ssDNA and RNA ligands to ICP4 which inhibit the function of ICP4. The scope of the ligands covered by this invention extends to all Nucleic Acid Ligands of ICP4, modified and unmodified, identified according to the SELEX procedure. More specifically, this invention includes Nucleic Acid sequences that are substantially homologous to the ligands shown in Table 5 (SEQ ID NOS: 17–57). By substantially homologous it is meant a degree of primary sequence homology in excess of 70%, most preferably in excess of 80%. A review of the sequence homologies of the ligands of ICP4 shown in Table 5 (SEQ ID NOS: 17–57) shows that sequences with little or no primary homology may have substantially the same ability to bind ICP4. For these reasons, this invention also includes Nucleic Acid Ligands that have substantially the same structure and ability to bind ICP4 as the Nucleic Acid Ligands shown in Tables 5 and 7–9 (SEQ ID NOS.: 17–57, 59–86). Substantially the same ability to bind ICP4 means that the affinity is within one or two orders of magnitude of the affinity of the ligands described herein. It is well within the skill of those of ordinary skill in the art to determine whether a given sequence—substantially homologous to those specifically described herein—has substantially the same ability to bind ICP4.

One potential problem encountered in the therapeutic and in vivo diagnostic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the Nucleic Acid Ligand can be made to increase the in vivo stability of the Nucleic Acid Ligand or to enhance or to mediate the delivery of the Nucleic Acid Ligand. See, e.g., U.S. patent application Ser. No. 08/117,991, filed Sep. 9, 1993, entitled High Affinity Nucleic Acid Ligands Containing Modified Nucleotides, which is specifically incorporated herein by reference. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post- SELEX modifications. Pre-SELEX modifications yield Nucleic Acid Ligands with both specificity for their SELEX Target and improved in vivo stability. Post-SELEX modifications made to 2'-OH Nucleic Acid Ligands can result in improved in vivo stability without adversely affecting the binding capacity of the Nucleic Acid Ligand.

Other modifications are known to one of ordinary skill in the art. Such modifications may be made post-SELEX (modification of previously identified unmodified ligands) or by incorporation into the SELEX process.

As described above, because of their ability to selectively bind ICP4, the Nucleic Acid Ligands to ICP4 described herein are useful as pharmaceuticals. This invention, therefore, also includes a method for treating herpes viruses by administration of a Nucleic Acid Ligand capable of binding to ICP4 or homologous proteins.

Therapeutic compositions of the Nucleic Acid Ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing Nucleic Acid Ligands for systemic delivery may be via subcutaneous, intramuscular, intravenous, intranasal or vaginal or rectal suppository.

In the Examples that follow, the use of SELEX methodology to identify high affinity DNA and RNA ligands to transcription regulatory factors is described.

The following Examples are provided to explain and illustrate the present invention and are not intended to be limiting of the invention. Example 1 describes the various materials and experimental procedures used in Examples 2 and 3. Example 2 describes the ssDNA ligands to ICP4. Example 3 describes the RNA ligands to ICP4. Example 4 describes binding competition between SELEX-derived ligands and DNA containing known ICP4 recognition sequences. Example 5 describes phosphorothioate-modified ssDNA ligands to ICP4. Example 6 describes modified 2'-NH₂ pyrimidine RNA ligands to ICP4.

EXAMPLE 1

Experimental Procedures

This example provides general procedures followed and incorporated in Examples 2 and 3 for the evolution of ssDNA and RNA ligands to ICP4.

A. Biochemicals

The truncated protein, FP505, containing residues 210–490 of the full-length ICP4 protein fused to a 43-residue polypeptide at the N-terminus to aid purification (Table 2; SEQ ID NO:5), was kindly provided by Kent Wilcox (Medical College of Wisconsin). The FP505 protein contains the DNA-binding/dimerization domain of ICP4 (67). The full-length ICP4 was a gift from Neil DeLuca (University of Pittsburgh School of Medicine). Oligodeoxynucleotides were synthesized by standard cyanoethyl phosphoramidite chemistry, and routinely purified to a homogeneous size by denaturing polyacrylamide gel electrophoresis before use.

B. ssDNA SELEX procedures

Radiolabeled single-stranded DNA (ssDNA) was routinely obtained by labeling the 5'-ends of gel-purified ssDNA with $\gamma$-$^{32}$P-ATP (NEN-DuPont), catalyzed by T4 polynucleotide kinase (New England Biolabs). ssDNA SELEX was initiated with 5 nmoles of a synthetic, gel-purified sequence library containing a 40 nucleotide randomized region (Table 3; SEQ ID NO:6). The fixed regions were specifically designed so that they do not contain any of the possible trimer sequences found in the ICP4 binding consensus. This was done to prevent the selection of hairpin-loops containing the consensus duplex in the fixed regions. In a typical round of SELEX, radiolabeled ssDNA pools were suspended in SELEX buffer (phosphate-buffered saline, (reference 51) containing 2 mM MgCl₂, pH 7.4). The ssDNA pools were then heated to 80° C. for 3 minutes, chilled on ice, and transferred to room temperature. Following equilibration to room temperature, ssDNA pools were diluted into binding buffer containing 100 μg human serum albumin (hSA) to prevent protein aggregation. ICP4 protein was then added to the ssDNA solutions and incubated at 37° C. for 30 minutes (rounds 1–10) or 15 minutes (rounds 11–13). Binding reactions were then filtered under suction through 0.45 μm nitrocellulose filters (Millipore), pre-wet with binding buffer. The filters were immediately washed with 20 ml of binding buffer. In rounds 3–13, 0.5M urea washes preceded the buffer washes (see below). For each binding reaction, a protein-minus control reaction was done in parallel in order to determine the amount of background binding to the filters. The amount of ssDNA retained on the filters was quantified by Cherenkov counting, and compared with the amount input into the reactions. Filter-retained ssDNA was extracted with phenol and chloroform, and isolated by ethanol precipitation in the presence of 5 μg carrier tRNA or glycogen.

The isolated ssDNA was amplified by the polymerase chain reaction (PCR) with specific primers (Table 3; SEQ ID NOS:7–8), one of which contained three contiguous biotins at its 5'-end. The unbiotinylated strand of the resulting duplex DNA was isolated by gel electrophoresis under denaturing conditions and purified for use in the next round of SELEX.

C. RNA SELEX procedures

RNA SELEX was done as described above for ssDNA with the following differences. RNA SELEX was initiated with 10 nmoles of a sequence library containing a 40 nucleotide randomized region sequence (Table 4; SEQ ID NO:12). The RNA library was transcribed from the corresponding synthetic DNA template (1 nmole) (SEQ ID NO:11) that was gel-purified and subjected to four rounds of PCR. The PCR-derived template (2 nmoles) was transcribed in ten 0.5 ml reactions, each containing 200 pmoles template, 0.58 μM T7 RNA polymerase, 2 mM each of NTPs, 40 U RNasin (Promega Corp.), 40 mM Tris-HCl (pH 8.0), 12 mM MgCl₂, 1 mM spermidine, 5 mM DTT, 0.002% Triton X-100 and 4% polyethylene glycol (w/v) for 2 hours at 37° C. Radiolabeled RNA was obtained from transcription reactions as described above, but containing 0.2 nM ATP and 100 μCi of $\alpha$-$^{32}$P-ATP. The full-length transcription products were routinely purified to a homogeneous size by denaturing polyacrylamide gel electrophoresis before use. RNasin was added to each binding reaction to prevent RNA degradation.

The filter-retained RNA was isolated as described for ssDNA above. The isolated RNA was subsequently used as a template for avian myeloblastosis virus reverse transcriptase (AMV-RT, Life Sciences) to obtain cDNA. One hundred pmoles of the 3'-primer Ib (Table 4; SEQ ID NO:14) was added to the RNA and annealed by heating for 3 minutes at 70° C., followed by chilling on ice. The 50 μl reaction contained 5 U AMV-RT, 0.4 mM each of dNTPs, 50 mM Tris-HCl (pH 8.3), 60 mM NaCl, 6 mM Mg(OAc)₂, and 10 mM DTT, which was incubated for 45 minutes at 48° C. The CDNA was amplified by PCR with the primer set Ib, and the resulting DNA template was transcribed to obtain RNA for the next round of SELEX.

D. SELEX strategies

Due to the small quantity of the full-length ICP4 protein that was available, the FP505 protein was used as the primary SELEX target. However, to ensure that the enriched oligonucleotide pools do recognize the full-length protein, the sixth and eighth rounds of both ssDNA and RNA SELEX were carried out with the full-length ICP4 protein. Following the rounds that targeted the full-length protein, the resulting pools exhibited improved binding to the FP505 protein, suggesting that the enriched oligonucleotides bind to a region in common to the two proteins, namely, the ICP4 DNA-binding domain.

The protein concentration in the binding reactions was 15 nM for the first round of SELEX, and was gradually decreased by increasing the reaction volume in subsequent rounds to exert selective pressure. The ratio of oligonucleotides to protein was at least 5:1 to ensure competition for high-affinity binding sequences. In addition, in rounds 3–13, the filters were washed with 10–80 ml of 0.5M urea, followed by the 20 ml binding buffer wash. This stringent washing procedure helped to remove non-specific nitrocellulose filter-binding sequences so that they would be eliminated during enrichment. Despite these precautions, nitrocellulose filter-binding sequences were slightly apparent by round nine. To counteract further accumulation of undesirable sequences, in rounds ten through thirteen the oligonucleotide pools were pre-soaked with nitrocellulose filters before incubating with the target protein. Post-soaking was also done following recovery of target-bound oligonucleotides, prior to amplification for the next round. This treatment worked well to reduce background with a concomitant increase in the proportion of high affinity binders in both ssDNA and RNA pools. The progress of SELEX was monitored by nitrocellulose filter-binding analysis of the enriched pools (see below).

E. Molecular cloning and DNA sequencing

To obtain individual high-affinity sequences from the enriched pools (round 12), PCR-amplification with primers (Tables 3 and 4, primer sets II; SEQ ID NOS:9–10, 15–16) was employed to engineer placement of HindIII and BamHI restriction sites at the termini of the resulting duplex DNA. This DNA was ethanol-precipitated and digested with HindIII and BamHI for cloning by standard procedures into plasmid vector pUC 19(69) that had been previously digested with the same enzymes. Clones were sequenced by the Sanger dideoxy method (Sequenase, US Biochemicals).

F. Nitrocellulose filter-binding

Labeled oligonucleotides were suspended in the binding buffer and heated to 80° C., chilled on ice and then transferred to room temperature. In binding reactions, oligonucleotide concentrations were kept between 10 and 50 pM to ensure equilibrium in conditions of protein excess. Oligonucleotides were incubated for 15 minutes at 37° C. with varying amounts of the FP505 protein in 60 μl of the binding buffer containing 0.01% hSA. Binding reactions were routinely done with and without inclusion of an excess (67 nM) of non-specific competitor tRNA (*E. coli*; Boehringer Mannheim). Binding reactions were then centrifuged for 3 minutes at 14,000 rpm. Fifty microliters of each binding mixture was carefully removed to avoid disturbing any aggregated material, and was placed on pre-wet 0.45 μm nitrocellulose filters under suction. Each filter was immediately washed with 5 ml binding buffer. The amount of radioactivity retained on the filters was quantitated by liquid scintillation counting. The radioactivity that bound to filters in the absence of protein was used for background correction. The percentage of input oligonucleotide retained on each filter was plotted against the corresponding log protein concentration. The nonlinear least square method was used to obtain the dissociation constant ($K_d$; (reference 32).

EXAMPLE 2 ssDNA Ligands to ICP4

A. ssDNA SELEX

During the course of SELEX, the enrichment of ssDNA oligonucleotides that bind ICP4 was monitored by nitrocellulose filter-binding. It was observed that the selected ssDNA pool derived from the twelfth round had a bulk $K_d$ of 2 nM versus>160 nM for the random pool. After the twelfth round, binding affinity to the target protein did not continue to improve. Therefore, individual ligands were isolated and characterized from the twelfth round ssDNA pool.

Individual sequences were grouped into three classes based on similarity (Table 5; SEQ ID NOS:17–57); analysis was aided by a computerized alignment program (31). Sequences in classes I and II have inverted repeats (indicated by half arrows in Table 5), suggesting that the ligands may form stem-loop structures. The predicted stem-loop structures are different in the two classes. The sequence and the number of nucleotides (nts) in the loop are fairly conserved in class I, but much less so in class II. The 10-nt loop in class I members contains the conserved sequence, 5'-TTTCA$_{/G}$CGT$_{/C}$AT-3' (SEQ ID NO:58). The base-pairing of the stem in class I sequences is uninterrupted, while that of most class II sequences is interrupted by a bulge or two non-complementary bases. The stems of the predicted stem-loops of all of class I and some of class II contain the sequence 5'-ATCGTC-3', which is the core of the naturally occurring consensus double-stranded DNA (dsDNA) sequence for ICP4 (11). Sequences belonging to class III apparently do not share any common secondary structural motifs.

Equilibrium dissociation constants ($K_d$ values) of several individual ligands of class I and II and a representative ligand from class III were determined by nitrocellulose filter-binding to the FP505 (SEQ ID NO:5) protein (Table 6). Except for the Class III sequence D.17, the rest of the classes I and II sequences have $K_d$ values of between 0.3 and 3.5 nM, indicative of tight binding to the FP505 protein.

The binding of the random ssDNA pool was quite sensitive to the presence of an 1000-fold excess of non-specific oligonucleotide competitor (tRNA) in the binding reactions. Calculated $K_d$ values for the random pool are >160 nM and >11 nM with and without tRNA, respectively. However, the binding of the ssDNA ligand D.5.36 (SEQ ID NO:59) was not significantly affected by the presence of tRNA. Calculated $K_d$ values for ligand D.5.36 (SEQ ID NO:59) are 0.6 nM and 0.3 nM with and without tRNA, respectively. A similar insensitivity to competition by excess tRNA was also observed with several other high-affinity SELEX-derived ligands (data not shown).

Interestingly, the presence of excess tRNA significantly reduced binding of FP505 (SEQ ID NO:5) protein to dsDNA oligonucleotides which contain a known ICP4 binding site. The two dsDNA oligonucleotides were 35 and 200 base-pairs, each containing an ICP4-binding sequence from the promoter region of the HSV-1 ICP0 gene promoter region (45). The sequence of the 35mer is 5'-CC-ATTGGGGGAATCGTCACTGCCGCCCCTTTGGGG-3' (SEQ ID NO:87). The 200mer is comprised of this sequence plus adjacent bases found in the ICP0 promoter region (45).

Calculated $K_d$ values for the 35mer are >1 μM and >30 nM, with and without tRNA, respectively. Calculated $K_d$ values for the 200mer are >1 μM and 0.5 nM, with and without tRNA, respectively. These results indicate that the SELEX-derived ligands are less susceptible to non-specific competition than are native ICP4 binding sites, at least under the conditions used in these binding studies.

B. Binding of ssDNA truncates

To investigate whether the predicted stem-loop structures are sufficient for high-affinity binding to ICP4, several ssDNA oligonucleotides were synthesized based on the SELEX-derived regions of class I and II sequences (Tables 7 and 8). These oligonucleotides were tested in binding assays to determine their affinities for the FP505 protein (results summarized in Tables 7 and 8; SEQ ID NOS:59–74). The data indicate that the SELEX-derived region of the class I sequence containing the predicted conserved stem-loop structure (D.5.36; SEQ ID NO:59) is sufficient for high-affinity binding to ICP4, and that the D.5 fixed regions are dispensable (see Table 6 for binding affinities of full-length ssDNA ligands). Further truncations of the presumably unpaired bases adjacent to the stem-loop of D.5.36 (SEQ ID NO:59) resulted in only slightly reduced binding affinity (see D.5.28 (SEQ ID NO:60) and D.5.24 (SEQ ID NO:61) in Table 7). From these data it can be inferred that most of the high-affinity binding of class I ssDNA ligands can be attributed to the core of the predicted stem-loop, rather than any adjacent bases. The high-affinity binding of another class I truncate (D.63.33; SEQ ID NO:63) is consistent with this assessment (Table 7). In addition, the D.32.31 (SEQ ID NO:62) truncate, which contains a single unpaired base that interrupts the conserved stem sequence (5'-ATCGT-3'), exhibited measurably lower binding than the other class I truncates (Table 7). This suggests that the class I consensus stem sequence is important for high-affinity binding.

Truncation of class II sequences yielded much less consistent or predictable results than those obtained with the class I truncates (Table 7). No clear correlation between the relative strengths of the predicted stem-loop structures and the binding affinities of the truncates were observed. For example, D.4.36 (SEQ ID NO:64) has a substantially better binding affinity compared to D.49.25 (SEQ ID NO:67), although the latter has a much stronger predicted stem. These data are complicated by the fact that the two sequences differ in length. The poor binding of D.25.34 (SEQ ID NO:65) does apparently correlate with a weak predicted stem structure (Table 7), but the binding of the full-length parent D25 ligand does not appear to be adversely affected by this weakness (Table 6). Taken together, these results indicate that sequence information other than that contained in the conserved stem-loops is required for high-affinity binding of class II ligands.

In order to investigate the involvement of the predicted loop and the stem of the D.5.36 (SEQ ID NO:59) sequence in high-affinity binding to the FP505 (SEQ ID NO:5) protein, several oligonucleotide constructs were synthesized in which either the stem or the loop was altered, and their binding affinities were determined (Table 8). Substituting the specific class I loop sequence (5'-TTTCGCGCAT-3'; SEQ ID NO: 58) with nine thymidine residues abolished the high-affinity binding to FP505 (compare D.5.36 (SEQ ID NO:59) and D.5.T-Loop (SEQ ID NO:68) in Table 8). This indicates that the specific base sequence in the loop is involved with the high-affinity binding of class I ligands, and that the presence of the consensus sequence in the stem is not sufficient to confer high-affinity binding. Similarly, the substitution of the loop sequence of class I in the sequence D.5.36 (SEQ ID NO:59) with that of class II also decreased the tight binding (D.5.LOOP:B; SEQ ID NO:70). This effect was also true for a class II sequence (D.49.25; SEQ ID NO:67) where the substitution of the loop with the class I loop reduced binding affinity (compare D.49.25 (SEQ ID NO:67) with D.49.LOOP:A (SEQ ID NO:72)). These data suggest that the conserved loop in each class functions well when located in the context of their respective stems. Extending of the stem did not seem to affect the high-affinity binding (D.5.EXT; SEQ ID NO:69). However, substituting 5-methyl-cytosines for the two C-residues in the stem of D.5.28 (SEQ ID NO:60) decreased its binding affinity by a factor of 20, suggesting that even a subtle change in the bases of the stem may affect binding to ICP4.

EXAMPLE 3

RNA Ligands to ICP4

A. RNA SELEX

As with the ssDNA SELEX, individual RNA ligands were isolated and characterized from the twelfth round pool. It was observed that the twelfth round pool binds to the FP505 (SEQ ID NO:5) protein with a $K_d$ of 0.1 nM, whereas the random RNA pool has a $K_d$ in excess of 100 nM. Cloning and sequencing of the twelfth round pool revealed essentially a single sequence with a few minor variants (Table 9; SEQ ID NOS:75–86). The binding affinities of several individual sequences were determined to be similar to that of the twelfth round pool (data not shown). The minor differences between sequences did not apparently exert a significant variation in binding affinity. Clone R.26 (SEQ ID NO:75) was chosen for further characterization because it was the most abundant individual sequence. In addition, the binding of high-affinity RNA ligands to FP505 (SEQ ID NO:5) exhibited a similar resistance to nonspecific competition by 1000-fold excess tRNA as did the ssDNA ligands (data not shown).

The SELEX-derived region of the RNA ligands consists of a purine-rich repeating pattern, consistent with that of G-quartet structures. The full-length R.26 (SEQ ID NO:75) sequence might fold into one of two possible secondary structures: a stem with a large unstructured loop, or a stem with the loop folded into a G-quartet structure (data not shown). An RNA oligonucleotide consisting solely of the random region of R.26 (SEQ ID NO:75) exhibited almost no binding to the FP505 protein (data not shown), indicating that bases in the fixed region(s) are important for binding.

The high affinities of the SELEX-derived ligands, combined with their observed competition with the native binding sequence, suggest that they have the capacity to occupy the DNA-binding site of ICP4. It can be inferred that occupancy of the DNA-binding site of ICP4 would inhibit its function, making the SELEX-derived ligands inhibitors of HSV proliferation.

EXAMPLE 4.

Binding Competition Between SELEX-Derived Ligands and DNA Containing Known ICP4 Recognition Sequences The conserved stem sequences in the SELEX-derived ssDNA ligands resemble the known ICP4 binding consensus, suggesting that the SELEX-derived ligands bind to the ICP4 protein DNA-binding site. In order to test this hypothesis, direct binding competition between the different ligands was employed (Table 10). Competition experiments utilized nitrocellulose filter-binding as described in Example 1, with the following exceptions: 1) the concentration of the labeled ligand was fixed at or near the ligand's $K_d$ value; 2) the protein concentration was fixed at the same value as the labeled ligand; and 3) the unlabeled competitor was titrated in a wide range bracketing the concentration of the labeled ligand.

A matrix of competition experiments was performed (Table 10). It was first determined that the labeled ligands were subject to self-competition, and that the $K_c$ values were equivalent to their respective $K_d$ values. The results of the competition experiments indicate that representative SELEX-derived ssDNA and RNA ligands compete with each other for binding to the FP505 protein. In addition, both ssDNA and RNA ligands compete for binding with duplex DNA oligonucleotides which contain the native ICP4 recognition sequence. The competition results strongly suggest that the different molecular species bind to the same or overlapping site(s) on the protein. Furthermore, these results suggest that the ICP4 protein preferentially bind to the SELEX-derived ligands in the presence of duplex DNA containing the ICP4 recognition sequence. This observation is consistent with the relative binding affinities of the SELEX-derived ligands versus those of the duplex DNA fragments carrying the consensus ICP4 binding site (e.g., 0.3 nM versus >30 nM), as well as the tRNA competition data (see Example 2).

Clusel and colleagues designed ssDNA hairpin oligonucleotides based on known duplex ICP4 binding sequences, which apparently inhibit ICP4 function (5). The best ICP4 inhibitor described in their study, hpIEX, was chosen for binding studies to compare with representative SELEX-derived ligands. In nitrocellulose-filter binding experiments with the FP505 protein, calcuated $K_d$ values for the hpIEX oligonucleotide were determined to be >500 nM and 20 nM, with and without 1000-fold excess tRNA, respectively (data not shown). These values are similar to those observed for a duplex DNA oligonucleotide of similar size containing a known ICP4 recognition sequence (see Example 3 above). In competition studies, both D.5.36 (SEQ ID NO:59) and R.26 (SEQ ID NO:75) competed with labeled hpIEX with $K_c$ values equal to their measured $K_d$ values, between 0.1 and 0.3 nM (Table 10).

EXAMPLE 5

Phosphorothioate-modified ssDNA Ligands to ICP4

Variations of the D.5.36 ligand (SEQ ID NO:59) were synthesized with phosphorothioate linkages substituted for all or some of the phosphodiester bonds. For example, ligand D.5.36.PT (SEQ ID NO:74), exhibited binding affinity to the FP505 protein (SEQ ID NO:5) similar to that of the best binding phosphodiester ligands (Table 8). Equivalent binding affinity was also observed with additional ligands that were all or partially phosphorothioated (data not shown). Some of these ligands were additionally modified to contain a 3' cap, which did not adversely affect binding affinity (data not shown).

EXAMPLE 6

Modified 2'-NH$_2$ pyrimidine RNA Ligands to ICP4

In order to generate ligands with improved stability in vitro, an experiment is carried out with randomized RNA containing amino (NH$_2$) functionalities at the 2'-position of each pyrimidine. A library of $10^{14}$ RNA molecules is generated that contains 40 nucleotides of contiguous random sequence flanked by defined sequences. Defined nucleotide sequences in the flanking regions of the template are designed so that they do not contain any of the possible primer sequences found in the ICP4 binding consensus. The random nucleotides of the initial Candidate Mixture are comprised of 2'-NH$_2$ pyrimidine bases. The rounds of selection and amplification are carried out as described supra in Example 1 using art-known techniques.

LITERATURE CITED

1. Bean, B. 1992. Antiviral therapy: current concepts and practices. Clin. Microbiol. Rev. 5:146–182.
2. Beard, P., S. Faber, K. Wilcox, and L. Pizer. 1986. Herpes simplex virus immediate early infected-cell polypeptide 4 binds to DNA and promotes transcription. Proc. Natl. Acad. Sci. USA. 83:4016–4020.
3. Cantin, E., G. Podsakoff, D. Willey, and H. Openshaw. 1992. Antiviral effects of herpes simplex virus specific anti-sense nucleic acids. Adv. Exp. Med. Biol. 312:139–49.
4. Cheung, A. 1989. DNA nucleotide sequence analysis of the immediate-early gene of pseudorabies virus. Nucleic Acids Res. 17:4637–4646.
5. Clusel, C., S. Meguenni, I. Elias, M. Vasseur, and M. Blumenfeld. 1995. Inhibition of HSV-1 proliferation by decoy phosphodiester oligonucleotides containing ICP4 recognition sequences. Gene Expression. 4:301–309.
6. Crooke, R., G. Hoke, and J. Shoemaker. 1992. In vitro toxicological evaluation of ISIS 1082, a phosphorothioate oligonucleotide inhibitor of herpes simplex virus. Antimicrob. Agents Chemother. 36:527–532.
7. Davison, A., and J. Scott. 1986. The complete DNA sequence of varicella-zoster virus. J. Gen. Virol. 67:1759–1816.
8. DeLuca, N., and P. Schaffer. 1987. Activities of herpes simplex virus type 1 (HSV-1) ICP4 genes specifying nonsense peptides. Nucleic Acids Res. 15:4491–4511.
9. DeLuca, N., and P. Schaffer. 1988. Physical and functional domains of the herpes simplex virus transcriptional regulatory protein ICP4. J Virol. 62:732–743.
10. DeLuca, N. A., A. M. McCarthy, and P. A. Schaffer. 1985. Isolation and characterization of deletion mutants of herpes simplex virus type 1 in the gene encoding immediate-early regulatory protein ICP4. J. Virol. 56:558–570.
11. Didonato, J. A., J. R. Spitzner, and M. T. Muller. 1991. A predictive model for DNA recognition by the herpes simplex virus protein ICP4. J. Mol. Biol. 219:451–470.
12. Disney, G. H., and R. D. Everett. 1990. A herpes simplex virus type 1 recombinant with both copies of the Vmw175 coding sequences replaced by the homologous varicella-zoster virus open reading frame. J. Gen. Virol. 71:2681–2690.
13. Disney, G. H., T. A. Mckee, C. M. Preston, and R. D. Everett. 1990. The product of varicella-zoster virus gene 62 autoregulates its own promoter. J. Gen. Virol. 71:2999–3004.
14. Draper, K., M. Ceruzzi, M. Kmetz, and L. Sturzenbecker. 1990. Complementary oligonucleotide sequence inhibits both Vmw65 gene expression and replication of herpes simplex virus. Antiviral Res. 13:151–164.
15. Everett, R., A. Cross, J. Tyler, and A. Orr. 1993. An epitope with the DNA-binding domain of the herpes simplex virus immediate early protein Vmw175 is conserved in the varicella-zoster virus gene 62 protein. J. Gen. Virol. 74:1955–1958.

16. Everett, R. D. 1988. Promoter sequence and cell type can dramatically affect the efficiency of transcriptional activation induced by herpes simplex virus type 1 and its immediate-early gene products Vmw175 and Vmw 110. J. Mol. Biol. 203:739–752.

17. Everett, R. D., J. Didonato, M. Elliott, and M. Muller. 1992. Herpes simplex virus type 1 polypeptide ICP4 bends DNA. . 20:1229–1233.

18. Everett, R. D., M. Elliott, G. Hope, and A. Orr. 1991. Purification of the DNA binding domain of herpes simplex virus type 1 immediate-early protein Vmw175 as a homodimer and extensive mutagenesis of its DNA recognition site. Nucleic Acids Res. 19:4901–4908.

19. Everett, R. D., T. Paterson, and M. Elliott. 1990. The major transcriptional regulatory protein of herpes simplex virus type 1 includes a protease resistant DNA binding domain. Nucleic Acids Res. 18:4579–4586.

20. Faber, S., and K. Wilcox. 1988. Association of herpes simplex virus regulatory protein ICP4 with sequences spanning the ICP4 gene transcription initiation site. Nucleic Acids Res. 16.

21. Felser, J. M., P. R. I(inchington, G. Inchauspe, S. E. Straus, and J. M. Ostrove. 1988. Cell lines containing varicella-zoster virus open reading frame 62 and expressing the IE 175 protein complement ICP4 mutants of herpes simplex virus type 1. J. Virol. 62:2076–2082.

22. Fennewald, S., S. Mustain, J. Ojwang, and R. Rando. 1995. Inhibition of herpes simplex virus in culture by oligonucleotides composed entirely of deoxyguanosine and thymidine. Antiviral Res. 26:37–54.

23. Field, A. K., and K. K. Biron. 1994. "The end of innocence" revisited: resistance of herpesviruses to antiviral drugs. Clin. Microbiol. Rev. 7:1–13.

24. Gao, W., R. Hanes, M. Vazquez-Padua, C. Stein, J. Cohen, and Y. Cheng. 1990. Inhibition of herpes simplex virus type 2 growth by phosphorothioate oligodeoxynucleotides. Antimicrob. Agents Chemother. 34:808–12.

25. Gao, W.-Y., J. W. Jaroszewski, J. S. Cohen, and Y.-C. Cheng. 1990. Mechanisms of inhibition of herpes simplex virus type 2 growth by 28-mer phosphorothioate oligodeoxycytidine. J. Biol. Chem. 265:20172–20178.

26. Gu, B., and N. A. DeLuca. 1994. Requirements for activation of the herpes simplex virus glycoprotein C promoter in vitro by the viral regulatory protein ICP4. J. Virol. 68:7953–7965.

27. Gu, B., R. Rivera-Gonzalez, C. Smith, and N. DeLuca. 1993. Herpes simplex virus infected cell polypeptide 4 preferentially represses Sp 1-activated over basal transcription from its own promoter. Proc Natl Acad Sci U S A. 90:9528–32.

28. Hoke, G., K. Draper, S. Freier, C. Gonzalez, V. Driver, M. Zounes, and D. Ecker. 1991. Effects of phosphorothioate capping on antisense oligonucleotide stability, hybridization and antiviral efficacy versus herpes simplex virus infection. Nucleic Acids Res. 19:5743–5748.

29. Imbalzano, A., A. Shepard, and N. DeLuca. 1990. Functional relevance of specific interactions between herpes simplex virus type 1 ICP4 and sequences from the promoter-regulatory domain of the viral thymidine kinase gene. J. Virol. 64:2620–2631.

30. Jacob, A., G. Duval-Valentin, D. Ingrand, N. Thuong, and C. Helene. 1993. Inhibition of viral growth by an alpha-oligonucleotide directed to the splice junction of herpes simplex virus type-1 immediate-early pre-mRNA species 22 and 47. Eur. J. Biochem. 216:19–24.

31. Javornik, B., and D. Zichi. 1995. Family identification and alignment of SELEX-isolated sequences. Manuscript in preparation.

32. Jellinek, D., C. K. Lynott, D. B. Rifkin, and N. Janjic. 1993. High-affinity RNA ligands to basic fibroblast growth factor inhibit receptor binding. Proc. Natl. Acad. Sci. USA. 90:11227–11231.

33. Kmetz, M. E., M. Ceruzzi, and J. Schwartz. 1991. Vmw65 phosphorothioate oligonucleotides inhibit HSV KOS replication and Vmw65 protein synthesis. Antiviral Res. 16:173–184.

34. Kuddus, R., B. Gu, and N. A. DeLuca. 1995. Relationship between TATA-binding protein and herpes simplex virus type 1 ICP4 DNA-binding sites in complex formation and repression of transcription. J. Virol. 69:5568–5575.

35. Kulka, M., C. Smith, L. Aurelian, R. Fishelevich, K. Meade, P. Miller, and P. Ts'o. 1989. Site specificity of the inhibitory effects of oligo(nucleoside methylphosphonate)s complementary to the acceptor splice junction of herpes simplex virus type1 immediate early mRNA 4. Proc. Natl. Acad. Sci. USA. 86:6868–6872.

36. Kulka, M., C. Smith, J. Levis, R. Fishelevich, J. Hunter, C. Cushman, P. Miller, P. Ts'o, and L. Aurelian. 1994. Synergistic antiviral activities of oligonucleoside methylphosphonates complementary to herpes simplex virus type 1 immediate-early mRNAs 4, 5, and 1. Antimicrob. Agents Chemother. 38:675–680.

37. Kulka, M., M. Wachsman, S. Miura, R. Fishelevich, P. Miller, P. Ts'o, and L. Aurelian. 1993. Antiviral effect of oligo(nucleoside methylphosphonates) complementary to the herpes simplex virus type 1 immediate early IRNAs 4 and 5. Antiviral Res. 20:115–130.

38. Matthews, J. T., B. J. Terry, and A. K. Field. 1993. The structure and function of the HSV DNA replication proteins: defining novel antiviral targets. Antiviral Res. 20:89–114.

39. McGeoch, D., A. Dolan, S. Donald, and D. Brauer. 1986. Complete DNA sequence of the short repeat region in the genome of herpes simplex virus type 1. Nucleic Acids Res. 14:1727–1745.

40. McGeoch, D. J., and S. Cook. 1994. Molecular phylogeny of the alphaherpesvirinae subfamily and a proposed evolutionary timescale. J. Mol. Biol. 238:9–22.

41. Olivo, P. D., N. L. Nelson, and M. D. Challberg. 1989. Herpes simplex virus type 1 gene products required for DNA replication: identification and overexpression. J. Virol. 63:196–204.

42. Oxman, M. N. 1992. Herpes simplex viruses and human herpesvirus 6, p. 1667–1700. In S. L. Gorbach and J. G. Bartell and N. R. Blacklow (ed.), Infectious Diseases. Saunders, Philadelphia.

43. Paterson, T., and R. D. Everett. 1988. Mutational dissection ofthe HSV-1 immediate-early protein Vmw 175 involved in transcriptional transactivation and repression. Virology. 166:186–196.

44. Paterson, T., and R. D. Everett. 1988. The regions of the herpes simplex virus type 1 immediate early protein Vmw175 required for site specific DNA binding closely correspond to those involved in transcriptional regulation. Nucleic Acids Res. 16:11005–11026.

45. Perry, L. J., F. J. Rixon, R. D. Everett, M. C. Frame, and D. J. McGeoch. 1986. Characterization of the IE110 gene of herpes simplex virus type 1. J. Gen. Virol. 67:2365–80.

46. Peyman, A., M. Helsberg, G. Kretzschmar, M. Mag, S. Grabley, and E. Uhlmann. 1995. Inhibition of viral growth by antisense oligonucleotides directed against the IE110 and the UL30 mRNA of herpes simplex virus type-1. Biol. Chem. Hoppe Seyler. 376:195–198.

47. Pizer, L., D. Tedder, J. Betz, and K. Wilcox. 1986. Regulation of transcription in vitro from herpes simplex virus genes. J. Virol. 60:950–959.
48. Pizer, L. I., R. D. Everett, D. G. Tedder, M. Elliott, and B. Litman. 1991. Nucleotides within both proximal and distal parts of the consensus sequence are important for specific DNA recognition by the herpes simplex virus regulatory protein ICP4. Nucleic Acids Res. 19:477–484.
49. Poddevin, B., S. Meguenni, I. Elias, M. Vasseur, and M. Blumenfeld. 1994. Improved anti-herpes simplex virus type 1 activity of a phosphodiester antisense oligonucleotide containing a 3'-terminal hairpin-like structure. Antisense Res. Dev. 4:147–154.
50. Roizman, B., and A. E. Sears. 1991. Herpes simplex viruses and their replication, p. 849–895. In B. N. Fields and D. M. Knipe (ed.), Fundamental Virology, 2nd ed. Raven Press, N.Y.
51. Sambrook, J., E. F. Fritsch, and T. Maniatis. 1989. Molecular Cloning. A Laboratory Manual, Second ed, vol. 3. Cold Spring Harbor Laboratory Press, Plainview, N.Y.
52. Shepard, A., and N. DeLuca. 1991. Activities of heterodimers composed of DNA-binding- and transactivation-deficient subunits of the herpes simplex virus regulatory protein ICP4. J. Virol. 65:299–307.
53. Shepard, A., and N. DeLuca. 1989. Intragenic complementation among partial peptides of herpes simplex virus regulatory protein ICP4. J. Virol. 63:1203–1211.
54. Shepard, A., and N. DeLuca. 1991. A second-site revertant of a defective herpes simplex virus ICP4 protein with restored regulatory activities and impaired DNA-binding properties. J. Virol. 65:787–795.
55. Shepard, A., A. Imbalzano, and N. DeLuca. 1989. Separation of primary structural components conferring autoregulation, transactivation, and DNA-binding properties to the herpes simplex virus transcriptional regulatory protein ICP4. J. Virol. 63:3714–3728.
56. Shepard, A., P. Tolentino, and N. DeLuca. 1990. trans-dominant inhibition of herpes simplex virus transcriptional regulatory protein ICP4 by heterodimer formation. J. Virol. 64:3916–3926.
57. Smith, C., L. Aurelian, M. Reddy, P. Miller, and P. Ts'o. 1986. Antiviral effect of an oligo(nucleoside methylphosphonate) complementary to the splice junction of herpes simplex virus type 1 immediate early pre-mRNAs 4 and 5. Proc. Natl. Acad. Sci. USA. 83:2787–2791.
58. Smith, C. A., and P. A. Schaffer. 1987. Intertypic recombinants of herpes simplex virus types 1 and 2 infected cell polypeptide 4. Virology. 160:176–182.
59. Tedder, D., R. Everett, K. Wilcox, P. Beard, and L. Pizer. 1989. ICP4-Binding sites in the promoter and coding regions of the herpes simplex virus gD gene contribute to activation of in vitro transcription by ICP4. J. Virol. 63:2510–252.
60. Tyler, J. K., K. E. Allen, and R. D. Everett. 1994. Mutation of a single lysine residue severely impairs the DNA recognition and regulatory functions of the VZV gene 62 transactivator protein. Nucleic Acids Res. 22:270–278.
61. Tyler, J. K., and R. D. Everett. 1993. The DNA binding domain of the varicella-zoster virus gene 62 protein interacts with multiple sequences which are similar to the binding site of the related protein of herpes simplex virus type 1. Nucleic Acids Res. 21:513–522.
62. Tyler, J. K., and R. D. Everett. 1994. The DNA binding domains of the varicella-zoster virus gene 62 and herpes simplex virus type 1 ICP4 transactivator proteins heterodimerize and bind to DNA. Nucleic Acids Res. 22:711–721.
63. Vinogradov, S., Y. Suzdaltseva, V. Alakhov, and A. Kabanov. 1994. Inhibition of herpes simplex virus 1 reproduction with hydrophobized antisense oligonucleotides. Biochem. Biophys. Res. Commun. 203:959–966.
64. Whitley, R. 1994. Herpes simplex virus infections of women and their offspring: implications for a developed society. Proc Natl Acad Sci U.S.A. 91:2441–7.
65. Whitley, R. J., and F. Lakeman. 1995. Herpes simplex virus infections of the central nervous system: therapeutic and diagnostic considerations. Clin. Infect. Dis. 20:414–420.
66. Whitton, J. 1994. Antisense treatment of viral infection. Adv. Virus Res. 44:267–303.
67. Wilcox, K. W. 1995. Personal communication.
68. Wu, C. L., and K. W. Wilcox. 1990. Codons 262 to 490 from the herpes simplex virus ICP4 gene are sufficient to encode a sequence-specific DNA binding protein. Nucleic Acids Res. 18:531–538.
69. Yanisch-Perron, C., J. Vieira, and J. Messing. 1985. Improved M13 phage cloning vectors and host strains: nucleotide sequences of the M13mp18 and pUC19 vectors. Gene. 33:103–119.

TABLE 1

| SEQ ID NO: | | | | |
|---|---|---|---|---|
| 2 | ICP4 (HSV) | 256 | R T P A A S A G R I - - E R R R A R A A V A G R D A T G R F T A G Q P R R V | 291 |
| 3 | gp62 (VZV) | 417 | R S I S G P D P R I R K T K R - - - - L A G E P G R Q R Q K S F S L P R S R | 450 |
| 4 | IE180 (PRV) | 458 | E P A R P P R R K R R S T N N H L S L M A D G P - - - - - - - - - - - - - | 481 |
| | ICP4 (HSV) | 292 | E L D A D A T S G A F Y A R Y R D G Y V S G E P W P G A G P P P P G R V L Y | 329 |
| | gp62 (VZV) | 451 | T P I I P P V S G P L M M P - - - - - - D G S P W P G S A P L P S N R V R F | 482 |
| | IE180 (PRV) | 482 | - - - - P P T D G P L L T P - - - - - - L G E P W P G S D P P A D G R V R Y | 509 |
| | ICP4 (HSV) | 330 | G G L G D S R P G L W G A P E A E E A R R R F E A S G A P A A V W A P E L G | 367 |
| | gp62 (VZV) | 483 | G P S G E T R E G H W E D E A V R A A R A R Y E A S T E P V P L Y V P E L G | 520 |
| | IE180 (PRV) | 510 | G G A G D S R E G L W D E D D V R Q A A A R Y R A A A G P V P V F I P E M G | 547 |
| | ICP4 (HSV) | 368 | D A A Q Q Y A L I T R L L Y T - P D A E A M G W L Q N P R V V P G D V A L D | 404 |
| | gp62 (VZV) | 521 | D P A R Q Y R A L I N L I Y C - P D R D P I A W L Q N P K L T G V N S A L N | 557 |
| | IE180 (PRV) | 548 | D S R K Q H E A L V R L I Y S G A A G E A M S W L Q N P R M Q A P D Q R F N | 585 |

TABLE 1-continued

| SEQ ID NO: | | | | |
|---|---|---|---|---|
| ICP4 (HSV) | 405 | Q A C F R I S G A A R N S S S F I T G S V A R A V P H L G Y A M A A G R F G | 442 |
| gp62 (VZV) | 558 | Q F Y Q K L L P P G R A - G T A V T G S V A S P V P H V G E A M A T G E A L | 594 |
| IE180 (PRV) | 586 | Q F C Q R V H A P H G H G S F I T G S V T P P L P H I G D A M A A Q D P L | 623 |
| | | | |
| ICP4 (HSV) | 443 | W G L A H A A A A V A M S R R Y D R A Q K G F L L T S L R R A Y A P L L A R | 480 |
| gp62 (VZV) | 595 | W A L P H A A A A V A M S R R Y D R A Q K H F I L Q S L R R A F A S M - - - | 629 |
| IE180 (PRV) | 624 | W A L P H A V S A V A M S R R Y D R T Q K T F I L Q S L R R A Y A D M - - - | 658 |
| | | | |
| ICP4 (HSV) | 481 | E N A A L T G A A G | 490 |
| gp62 (VZV) | 630 | - - - - - - - A Y P | 632 |
| IE180 (PRV) | 659 | - - - - - - - A Y P | 661 |

TABLE 2

SEQ ID NO:

1  mas mt g g q q m g r g s g s m g h h h h h h h h h s s g h i e g r h m l e g s P A D H A R E A R A V G R G P S S A  60

61  A P A A P G R T P P P P G P P P L S E A A P K P R A A A R T P A A S A G R I E R R R A R A A V A G R D A T G R F T A G Q  120

121  P R R V E L D A D A T S G A F Y A R Y R D G Y V S G E P W P G A G P P P P G R V L Y G G L G D S R P G L W G A P E A E E  180

181  A R R R F E A S G A P A A V W A P E L G D A A Q Q Y A L I T R L L Y T P D A E A M G W L Q N P R V V P G D V A L D Q A C  240

241  F R I S G A A R N S S S F I T G S V A R A V P H L G Y A M A A G R F G W G L A H A A A A V A M S R R Y D R A Q K G F L L  300

301  T S L R R A Y A P L L A R E N A A L T G A A G  323

TABLE 3

| SEQ ID NO: | For ssDNA SELEX: |
|---|---|
| | Starting random sequence DNA pool: |
| 6 | 5'-GGGAGGACAGTGCGG-[N]$_{40}$-CAGTGCGTCAGTCAAC-3' |
| | Primer set I: |
| 7 | 5'-PRIMER Ia: 5'-GGGAGGACAGTGCGG-3' |
| 8 | 3'-PRIMER Ia: 5'-B-B-B-GTTGACTGACGCACTG-3' (B = biotin) |
| | Primer set II: |
| 9 | 5'-PRIMER IIa: 5'-ACC<u>AAGCTT</u>GGGAGGACAGTGCGG-3' HindIII |
| 10 | 3'-PRIMER IIa: 5'-CGC<u>GGATCC</u>GTTGACTGACGCACTG-3' BamHI |

TABLE 4

| SEQ ID NO: | For RNA SELEX: |
|---|---|
| | Synthetic DNA template: |
| 11 | 5'-TAATACGACTCACTATAGGGAGACAAGAATAAACGCTCAA-[N]40-TTCGACAGGAGGCTCACAACAGGC-3' |

TABLE 4-continued

| SEQ ID NO: | For RNA SELEX: |
|---|---|
| | Starting random sequence RNA pool: |
| 12 | 5'-GGGAGACAAGAAUAAACGCUCAA-[N]40-UUCGACAGGAGGCUCACAACAGGC-3' |
| | Primer set I: |
| 13 | 5'-PRIMER Ib: 5'-TAATACGACTCACTATAGGGAGACAA-3' |
| 14 | 3'-PRIMER Ib: 5'-GCCTGTTGTGAGCCTCCTGTCGAA-3' |
| | Primer set II: |
| 15 | 5'-PRIMER IIb: 5'-CAGAAGCTTAATACGACTCACTATAGGGAGACAAGAATAAACGCTCAA-3'<br>             HindIII |
| 16 | 3'-PRIMER IIb: 5'GACTGGATCCGCCTGTTGTGAGCCTCCTGTCGAA-3'<br>            BamHI |

TABLE 5

Sequences of ssDNA clones from round 12-ICP4 SELEX.

5' - GGGAGGACAGTGCGG - 40N - CAGTGCGTCAGTCAAC - 3'

CLASS I

| SEQ ID NO: | | |
|---|---|---|
| 17 | D.5 | CCCTTATACGATTTTCGCGCATATCGTATCCCGCCGCCTT |
| 18 | D.9 | CCCATGATTTTCTTTGACGATTTTCACGTATATCGTCTC |
| 19 | D.10 | CCACTCACGATTTTCGCGTATATCGTCCCTCCTGCTTTTG |
| 20 | D.12 | CCATGTTTCTTATCGTGACGATTTTCGCGTATATCGTCG |
| 21 | D.13 | TCTCCCGTACGATTTTCACGCATATCGTACCCTGCTGCTG |
| 22 | D.14 | CCCAGATGGGTGTCATACGATTTTCACGTATATCGTATTT |
| 23 | D.18 | CCCGGCGATTTTCACGTATATCGCCCACCTGTTGAGTCTT |
| 24 | D.30 | CGCCTACATGTGCGAACGATTTTCACGCATATCGTTTTGC |
| 25 | D.32 (2) | CCAATGCCACTCTGATAACGATTTTCACGTATATCGGTGT |
| 26 | D.38 | GGCAACCGTAAACTACGATTTTCGCGTATATCGTAGTATG |
| 27 | D.55 | CGGCCCACTTCGTTCCCCCGACGATTTTCGCGTATATCGTCGC |
| 28 | D.63 | CGCCTACACCACGATTTTCACGCATATCGTGGTACCTTTT |
| 29 | D.31 | CCAGATATTAAACGATTTCACGCATATCGTTTAGTACA |
| 30 | D.24 | CCACATCACGCAGACGACCGTCATTTTCACGCATATCGTCCCTT |

TABLE 5-continued

Sequences of ssDNA clones from round 12-ICP4 SELEX.

5' - GGGAGGACAGTGCGG - 40N - CAGTGCGTCAGTCAAC - 3'

| SEQ ID NO: | | |
|---|---|---|
| | | CLASS II |
| 31 | D.3 | CCCTGCTGTTTCCGTGATCGTCAGGTAAGACCGATCGTCA |
| 32 | D.15 | CTGGATCGTATGGCAATAT GATCCCCCACCCCATCCGTCT |
| 33 | D.22 | TCACGTGTACCATCGTCTGGGAATAC GATGCTTTTTTGTC |
| 34 | D.27 | CACAAGACCTCGATCGTATGGTAATATCGATCTCCTTCGA |
| 35 | D.36 | TCCCGCGGCGCATCGTCTGGCAATAC GATGTCATGGCTTA |
| 36 | D.37 | CCGGCTTACTATGTGATCGTATGGAATAT GATCTTATTG |
| 37 | D.41 | CACGAACTTTCATCGTATGGGAATAT GATGTTTTCTTT |
| 38 | D.46 | CCATCTCAGATCGTATGGTAATATTGATCTTCTTGCACCT |
| 39 | D.1 | CCACACCCACCCATCGCCTGGTAATGC GATGTTCCCGGAC |
| 40 | D.4 | CCCCACGCAATATCGCATGGTAATGCCGATTACTACCATG |
| 41 | D.20 | TGCCCTGAATCGCTTGGTAATGC GACGCAGCCATTATGGT |
| 42 | D.25 | CGTGACGTATGGTATGGTAATACCGATCTTGTCCCGCAA |
| 43 | D.28 | CCCTTTACGATCGCATGGTAATGCTGATCCTATATTCCCC |
| 44 | D.45 | CGTGACGTATC TATGGTAATACCGATCTTATCCCGCAA |
| 45 | D.49 | GGGGATCGTCTGGTAATAC GATACCTGTTTTTCAATGCT |
| 46 | D.51 | GGGGCTGGTGAGCACATCGTATGGCAATAC GATGCTTATA |
| 47 | D.54 | CGGCCGGCTACCTGCTGATATCGTATGGTAATAT GATTGTACA |
| 48 | D.56 | CGGCCTTAGTGATCGTCTGGTAATAC GATCCTCTTTGCTGCACG |
| 49 | D.58 | CACAGGCATCGTATGGGAATACCGATGCTTCCGTAATTCA |
| 50 | D.62 | CCACCATGATCGTATGGGAATATTGATCTCCTGTCGGCTA |
| 51 | D.65 | CCACCATCGTATGGTAATACTGATGTTCCCATGTGCGGG |
| 52 | D.7 | CCCCTCGATCGTATGGGAATACCGATCACGATTTTCGCG |
| | | CLASS III |
| 53 | D.2 | TAGGGTAAGTGGTGTGTAAATTCTAGCCCCATCATCTGTG |
| 54 | D.17 | CTGTGGTTGAAGAAGTGGACGTCGTGGGATCGGGA |
| 55 | D.57 | TGACAATGTTGTCGGGGTTCGATGACCATGTGTAT |
| 56 | D.8 | GCAGGAGGTCAGCTGAGGTCGGAAGAGTGCTAGG |
| 57 | D.39 | TCCTTGGTGTGGATATGGGGGAACGGTTCGACCGA |

TABLE 6

Screening of ssDNA ligands for binding to the FP505 protein.

| | Clone Number | $K_d$ (nM)[a] |
|---|---|---|
| Class I | 5 | 0.3 ± 0.01 |
| | 9 | 0.6 ± 0.1 |
| | 10 | 1.5 ± 0.2 |
| | 13 | 1.5 ± 0.4 |
| | 31 | 1.2 ± 0.3 |
| | 35 | 1.5 ± 0.3 |
| | 55 | 0.3 ± 0.1 |
| Class II | 1 | 0.3 ± 0.1 |
| | 15 | 3.3 ± 0.7 |
| | 25 | 1.6 ± 0.6 |
| | 27 | 2.0 ± 0.4 |
| | 36 | 0.7 ± 0.3 |
| | 41 | 0.5 ± 0.1 |
| Class III | 17 | 18 ± 4.5 |

[a]Binding dissociation constants determined as described in Example 1.

TABLE 7

Binding of truncated ssDNA ligands to the FP505 protein.

| SEQ. ID NO: | ssDNA[a] | Sequence (5'-3')[b] | Length | $K_d$ (nM)[c] |
|---|---|---|---|---|
| *Class I* | | | | |
| 59 | D.5.36 | CCCTTATACGATTTTCGCGCATATCGTATCCCGCCG | 36 | 0.3 |
| 60 | D.5.28 | TTATACGATTTTCGCGCATATCGTATCC | 28 | 0.6 |
| 61 | D.5.24 | ATACGATTTTCGCGCATATCGTAT | 24 | 1.0 |
| 62 | D.32.31 | CTCTGATAACGATTTTCACGTATATCGGTGT | 31 | 3.7 |
| 63 | D.63.33 | TACACCACGATTTTCACGCATATCGTGGTACCT | 33 | 0.8 |
| *Class II* | | | | |
| 64 | D.4.36 | CCCCACGCAATATCGCATGGTAATGCCGATTACTAC | 36 | 1.1 |
| 65 | D.25.34 | CGTGACGTATGGTATGGTAATACCGATCTTGTCC | 34 | 280 |
| 66 | D.46.36 | CCATCTCAGATCGTATGGTAATATTGATCTTCTTGC | 36 | 2.6 |
| 67 | D.49.25 | GGGGATCGTCTGGTAATACGATCCC | 25 | 20 |

[a]Synthetic single-stranded oligodeoxynucleotides.
[b]Underlined bases indicate predicted base-paired (stem) regions.
[c]Binding dissociation constants determined as described in Example 1.

TABLE 8

Binding of truncated and modified ssDNA ligands to the FP505 protein.

| SEQ ID NO: | ssDNA[a] | Sequence (5'-3')[b] | Length | $K_d$ (nM)[c] |
|---|---|---|---|---|
| 59 | D.5.36 | CCCTTATACGATTTTCGCGCATATCGTATCCCGCCG | 36 | 0.3 |
| 68 | D.5.T-loop | GGGCCCATACGATTTTTTTTTATCGTATGGGCCC | 35 | 200 |
| 69 | D.5.EXT. | GGGCCCATACGATTTTCGCGCATATCGTATGGGCCC | 36 | 0.8 |
| 70 | D.5.LOOP:B | CCCTTATACGACTGGTAATATCGTATCCCGCCG | 33 | 20 |
| 71 | D.5.LOOP:GGTA | CCCTTATACGAGGTATCGTATCCCGCCG | 28 | >1000 |
| 67 | D.49.25 | GGGGATCGTCTGGTAATACGATCCC | 25 | 20 |
| 72 | D.49.LOOP:A | GGGGATCGTTTTCGCGCATACGATCCC | 27 | >300 |
| 60 | D.5.28 | TTATACGATTTTCGCGCATATCGTATCC | 28 | 0.6 |
| 73 | D.5.28methyl[d] | TTATACGATTTTCGCGCATATCGTATCC | 28 | 12 |
| 74 | D.5.36.PT[e] | tataTTATACGATTTTCGCGCATATCGTATCctatA | 36 | 0.2 |

[a]Synthetic single-stranded oligodeoxynucleotides.
[b]Underlined bases indicate predicted base-paired (stem) regions.
[c]Binding dissociation constants determined as described in Example 1.
[d]Italicized c indicates C5-methyl-dC.
[e]Lower case indicates phosphorothioate linkage.

TABLE 9

Sequences of RNA clones from round 12-ICP4 SELEX.

5'-GGGAGACAAGAAUAAACGCUCAA-[N]40-UUCGACAGGAGGCUCACAACAGGC-3'

| SEQ ID NO: | | |
|---|---|---|
| 75 | R26 (6) | AAGAACCAAAGGGAAGGGGGAAGAGGGAAGAGGGAUGUGG |
| 76 | R22 (2) | AAGAACCAAAGGGAAGGGGGAAGAGGGAAGCGGGAUGUGG |
| 77 | R28 (2) | AAGAACCAAAGGGAAGAGGGAAGAGGGAAGAGGGAUGUGG |
| 78 | R18 | AAGAACCAAAGGGAAGGGGGAAGAGGGAAGAGGGAUGUGG |
| 79 | R29 | AAGAACCAAUGGGAAGAGGGAAGAGGUAAGAGGGAUGUGG |
| 80 | R30 | AGGAACCAAAGGGAAGAGGGAAGAGGGACGAGGGAUGUGG |
| 81 | R31 | AAGAACCAAAGGGAAGAGGGAAGAGGGAAGCGGGAUGAGG |
| 82 | R32 | AAGAACCAAAGGGAAGGGGGAAGAGGGAAGAGGGAUGAGG |
| 83 | R35 | AGGAACCAAAGGGAAGGGGGAAGAGGGAAGAGGGAUGUGG |
| 84 | R36 | AAGAACCAAAGGGAAAAGGGAAGAGGGAAGAGGGAUGUGG |
| 85 | R40 | AAGAACCAAAGGGAAGAGGGAAGAGGGAAGCGGGAUGUGG |
| 86 | R45 | AGAACCGAAGGGAAGAGGGAAGAGGGAAGAGGGAUGAGG |

TABLE 10

Competition Matrix

| COMPETITOR | SEQ ID NO. | $K_d$ | LABELED SPECIES | | | | |
|---|---|---|---|---|---|---|---|
| | | | D.5.36 | R.26 | ds35 | ds200 | hpIEX |
| D.5.36 | 68 | 0.3 | +[a] | + | + | + | + |
| R.26 | 80 | 0.2 | + | + | | + | + |
| duplex 35mer | 87 | 30[b] | — | | | | |
| duplex 200mer | | 0.5[b] | — | — | | + | |
| hpIEX | | 20[b] | + | | | + | + |

[a] A plus sign (+) indicates that the competitor competed for binding with the labeled species; the competition equilibrium constants ($K_c$ values) for each competitor were equivalent to their respective $K_d$ values. A minus sign (−) indicates that the competitor did not compete for binding with the labeled species.
[b] $K_d$ values were determined in the absence of excess non-specific competitor tRNA. Note that excess tRNA significantly increases the $K_d$ values of the indicated species (see EXAMPLE 2).

---

We claim:

1. A method of identifying nucleic acid ligands to an ICP4 protein family member, comprising:
    a) preparing a candidate mixture of nucleic acids;
    b) contacting the candidate mixture of nucleic acids with an ICP4 protein family member, wherein nucleic acids having an increased affinity to an ICP4 protein family member relative to the candidate mixture may be partitioned from the remainder of the candidate mixture;
    c) partitioning the increased affinity nucleic acids from the remainder of the candidate mixture; and
    d) amplifying the increased affinity nucleic acids to yield a mixture of nucleic acids enriched for nucleic acid sequences with relatively higher affinity and specificity for binding an ICP4 protein family member, wherein nucleic acid ligands of an ICP4 protein family member may be identified.

2. The method of claim 1 further comprising:
    e) repeating steps b), c), and d).

3. The method of claim 1 wherein the ICP4 protein family member is ICP4.

4. The method of claim 1 wherein said candidate mixture of nucleic acids is comprised of single stranded nucleic acids.

5. The method of claim 1 wherein said candidate mixture of nucleic acids is comprised of single stranded ribonucleic acids.

6. The method of claim 1 wherein said candidate mixture of nucleic acids is comprised of single stranded deoxyribonucleic acids.

7. The method of claim 1 wherein said candidate mixture of nucleic acids is comprised of double stranded nucleic acids.

8. A purified and isolated non-naturally occurring nucleic acid ligand to a Transcription Regulatory Factor identified according to the method of claim 1.

9. A purified and isolated non-naturally occurring nucleic acid ligand to ICP4.

10. The nucleic acid ligand to ICP4 of claim 10 identified according to the method of claim 1.

11. The nucleic acid ligand to ICP4 of claim 10 identified according to the method of claim 2.

12. The nucleic acid ligand of claim 10, wherein said ligand is ssDNA selected from the group consisting of the sequences set forth in Tables 5 and 7–8 (SEQ ID NOS:17–57, 59–74).

13. The nucleic acid ligand of claim 10, wherein said ligand is an RNA selected from the group consisting of the sequences set forth in Table 9 (SEQ ID NOS:75–86).

* * * * *

UNITED STATES PATENT AND TRADEMARK OFFICE
CERTIFICATE OF CORRECTION

PATENT NO. : 5,795,721
DATED : August 18, 1998
INVENTOR(S) : Ross S. Rabin, Sumedha D. Jayasena and Larry Gold It is certified that error appears in the above-identified patent and that said Letters Patent is hereby corrected as shown below:

At col. 2, line 41, please delete "daltons" and insert --daltons.--.
At col. 4, line 19, before "Nucleic" please insert --Methods for Identifying--.
At col. 5, line 1, please delete "Methods of Producing".
At col. 5, line 1, after "Ligands" please insert --to HIV-RT and HIV-1 Rev--.
At col. 5, line 7, before "describes" please insert --now United States Patent No. 5,705,337,--.
At col. 5, line 40, before "respectively" please insert --now United States Patent No. 5,683,867,--.
At col. 5, line 64, please delete "Table" and insert --Tables--.
At col. 6, line 28, please delete "ICP4" and insert --ICP4.--. (2nd occurrence).
At col. 7, line 64, before "Nucleic" please insert --Methods for Identifying--.
At col. 8, line 53, before "enriched" please insert --an--.
At col. 9, lines 51-52, please delete "Methods of Producing Nucleic Acid Ligands" and insert --Nucleic Acid Ligands to HIV-RT and HIV-1 Rev--.
At col. 17, line 34, please delete "calcuated" and insert --calculated--.
At col. 23, in Table 2, after "SEQ ID NO:" please insert --5--.

Signed and Sealed this

Twentieth Day of April, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 87

( 2 ) INFORMATION FOR SEQ ID NO:1:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( x i ) SEQUENCE DESCRIPTION: SEQ ID NO:1:

RTCGTCNNYN YSG        13

( 2 ) INFORMATION FOR SEQ ID NO:2:

( i ) SEQUENCE CHARACTERISTICS:
        ( A ) LENGTH: 235
        ( B ) TYPE: amino acid ( C ) STRANDEDNESS: single
( D ) TOPOLOGY: linear ( x i ) SEQUENCE DESCRIPTION: SEQ ID NO:2:

| Arg | Thr | Pro | Ala | Ala | Ser | Ala | Gly | Arg | Ile | Glu | Arg | Arg | Arg |
|-----|-----|-----|-----|-----|-----|-----|-----|-----|-----|-----|-----|-----|-----|
|     |     |     |     | 5   |     |     |     |     | 10  |     |     |     |     |
| Ala | Arg | Ala | Ala | Val | Ala | Gly | Arg | Asp | Ala | Thr | Gly | Arg | Phe |
| 15  |     |     |     |     | 20  |     |     |     |     | 25  |     |     |     |
| Thr | Ala | Gly | Gln | Pro | Arg | Arg | Val | Glu | Leu | Asp | Ala | Asp | Ala |
|     | 30  |     |     |     |     | 35  |     |     |     |     | 40  |     |     |
| Thr | Ser | Gly | Ala | Phe | Tyr | Ala | Arg | Tyr | Arg | Asp | Gly | Tyr | Val |
|     |     | 45  |     |     |     |     | 50  |     |     |     |     | 55  |     |
| Ser | Gly | Glu | Pro | Trp | Pro | Gly | Ala | Gly | Pro | Pro | Pro | Pro | Gly |
|     |     |     | 60  |     |     |     |     | 65  |     |     |     |     | 70  |
| Arg | Val | Leu | Tyr | Gly | Gly | Leu | Gly | Asp | Ser | Arg | Pro | Gly | Leu |
|     |     |     |     | 75  |     |     |     |     | 80  |     |     |     |     |
| Trp | Gly | Ala | Pro | Glu | Ala | Glu | Glu | Ala | Arg | Arg | Arg | Phe | Glu |
| 85  |     |     |     |     | 90  |     |     |     |     | 95  |     |     |     |
| Ala | Ser | Gly | Ala | Pro | Ala | Ala | Val | Trp | Ala | Pro | Glu | Leu | Gly |
|     | 100 |     |     |     |     | 105 |     |     |     |     | 110 |     |     |
| Asp | Ala | Ala | Gln | Gln | Tyr | Ala | Leu | Ile | Thr | Arg | Leu | Leu | Tyr |
|     |     | 115 |     |     |     |     | 120 |     |     |     |     | 125 |     |
| Thr | Pro | Asp | Ala | Glu | Ala | Met | Gly | Trp | Leu | Gln | Asn | Pro | Arg |
|     |     |     | 130 |     |     |     |     | 135 |     |     |     |     | 140 |
| Val | Val | Pro | Gly | Asp | Val | Ala | Leu | Asp | Gln | Ala | Cys | Phe | Arg |
|     |     |     |     | 145 |     |     |     |     | 150 |     |     |     |     |
| Ile | Ser | Gly | Ala | Ala | Arg | Asn | Ser | Ser | Ser | Phe | Ile | Thr | Gly |
| 155 |     |     |     |     | 160 |     |     |     |     | 165 |     |     |     |
| Ser | Val | Ala | Arg | Ala | Val | Pro | His | Leu | Gly | Tyr | Ala | Met | Ala |
|     | 170 |     |     |     |     | 175 |     |     |     |     | 180 |     |     |
| Ala | Gly | Arg | Phe | Gly | Trp | Gly | Leu | Ala | His | Ala | Ala | Ala | Ala |
|     |     | 185 |     |     |     |     | 190 |     |     |     |     | 195 |     |
| Val | Ala | Met | Ser | Arg | Arg | Tyr | Asp | Arg | Ala | Gln | Lys | Gly | Phe |
|     |     |     | 200 |     |     |     |     | 205 |     |     |     |     | 210 |
| Leu | Leu | Thr | Ser | Leu | Arg | Arg | Ala | Tyr | Ala | Pro | Leu | Leu | Ala |
|     |     |     |     | 215 |     |     |     |     | 220 |     |     |     |     |
| Arg | Glu | Asn | Ala | Ala | Leu | Thr | Gly | Ala | Ala | Gly |     |     |     |
| 225 |     |     |     |     | 230 |     |     |     |     |     |     |     |     |

( 2 ) INFORMATION FOR SEQ ID NO:3:

( i ) SEQUENCE CHARACTERISTICS:
( A ) LENGTH: 216
( B ) TYPE: amino acid
( C ) STRANDEDNESS: single
( D ) TOPOLOGY: linear ( x i ) SEQUENCE DESCRIPTION: SEQ ID NO:3:

| Arg | Ser | Ile | Ser | Gly | Pro | Asp | Pro | Arg | Ile | Arg | Lys | Thr | Lys |
|-----|-----|-----|-----|-----|-----|-----|-----|-----|-----|-----|-----|-----|-----|
|     |     |     |     | 5   |     |     |     |     | 10  |     |     |     |     |
| Arg | Leu | Ala | Gly | Glu | Pro | Gly | Arg | Gln | Arg | Gln | Lys | Ser | Phe |
| 15  |     |     |     |     | 20  |     |     |     |     | 25  |     |     |     |
| Ser | Leu | Pro | Arg | Ser | Arg | Thr | Pro | Ile | Ile | Pro | Pro | Val | Ser |
|     | 30  |     |     |     |     | 35  |     |     |     |     | 40  |     |     |
| Gly | Pro | Leu | Met | Met | Pro | Asp | Gly | Ser | Pro | Trp | Pro | Gly | Ser |
|     |     | 45  |     |     |     |     | 50  |     |     |     |     | 55  |     |
| Ala | Pro | Leu | Pro | Ser | Asn | Arg | Val | Arg | Phe | Gly | Pro | Ser | Gly |

```
                  60                         65                             70
Glu  Thr  Arg  Glu  Gly  His  Trp  Glu  Asp  Glu  Ala  Val  Arg  Ala
                    75                      80

Ala  Arg  Ala  Arg  Tyr  Glu  Ala  Ser  Thr  Glu  Pro  Val  Pro  Leu
85                       90                      95

Tyr  Val  Pro  Glu  Leu  Gly  Asp  Pro  Ala  Arg  Gln  Tyr  Arg  Ala
         100                      105                     110

Leu  Ile  Asn  Leu  Ile  Tyr  Cys  Pro  Asp  Arg  Asp  Pro  Ile  Ala
              115                      120                          125

Trp  Leu  Gln  Asn  Pro  Lys  Leu  Thr  Gly  Val  Asn  Ser  Ala  Leu
              130                      135                          140

Asn  Gln  Phe  Tyr  Gln  Lys  Leu  Leu  Pro  Pro  Gly  Arg  Ala  Gly
                    145                     150

Thr  Ala  Val  Thr  Gly  Ser  Val  Ala  Ser  Pro  Val  Pro  His  Val
155                      160                     165

Gly  Glu  Ala  Met  Ala  Thr  Gly  Glu  Ala  Leu  Trp  Ala  Leu  Pro
     170                      175                     180

His  Ala  Ala  Ala  Ala  Val  Ala  Met  Ser  Arg  Arg  Tyr  Asp  Arg
          185                      190                          195

Ala  Gln  Lys  His  Phe  Ile  Leu  Gln  Ser  Leu  Arg  Arg  Ala  Phe
               200                     205                          210

Ala  Ser  Met  Ala  Tyr  Pro
                    215
```

( 2 ) INFORMATION FOR SEQ ID NO:4:

( i ) SEQUENCE CHARACTERISTICS:
        ( A ) LENGTH: 204
        ( B ) TYPE: amino acid
        ( C ) STRANDEDNESS: single
        ( D ) TOPOLOGY: linear ( x i ) SEQUENCE DESCRIPTION: SEQ ID NO:4:

```
Glu  Pro  Ala  Arg  Pro  Pro  Arg  Arg  Lys  Arg  Arg  Ser  Thr  Asn
                    5                       10

Asn  His  Leu  Ser  Leu  Met  Ala  Asp  Gly  Pro  Pro  Thr  Asp
15                       20                      25

Gly  Pro  Leu  Leu  Thr  Pro  Leu  Gly  Glu  Pro  Trp  Pro  Gly  Ser
     30                       35                      40

Asp  Pro  Pro  Ala  Asp  Gly  Arg  Val  Arg  Tyr  Gly  Gly  Ala  Gly
          45                      50                           55

Asp  Ser  Arg  Glu  Gly  Leu  Trp  Asp  Glu  Asp  Val  Arg  Gln
              60                      65                       70

Ala  Ala  Ala  Arg  Tyr  Arg  Ala  Ala  Ala  Gly  Pro  Val  Pro  Val
                    75                          80

Phe  Ile  Pro  Glu  Met  Gly  Asp  Ser  Arg  Lys  Gln  His  Glu  Ala
85                       90                           95

Leu  Val  Arg  Leu  Ile  Tyr  Ser  Gly  Ala  Ala  Gly  Glu  Ala  Met
     100                     105                     110

Ser  Trp  Leu  Gln  Asn  Pro  Arg  Met  Gln  Ala  Pro  Asp  Gln  Arg
              115                     120                          125

Phe  Asn  Gln  Phe  Cys  Gln  Arg  Arg  Val  His  Ala  Pro  His  Gly
              130                     135                          140

His  Gly  Ser  Phe  Ile  Thr  Gly  Ser  Val  Thr  Pro  Pro  Leu  Pro
                    145                     150

His  Ile  Gly  Asp  Ala  Met  Ala  Ala  Gln  Asp  Pro  Leu  Trp  Ala
```

| | | 155 | | | 160 | | | | 165 | | |
|---|---|---|---|---|---|---|---|---|---|---|---|
| Leu | Pro | His | Ala | Val | Ser | Ala | Val | Ala | Met | Ser | Arg | Arg | Tyr |
| | | 170 | | | 175 | | | | 180 | | |
| Asp | Arg | Thr | Gln | Lys | Thr | Phe | Ile | Leu | Gln | Ser | Leu | Arg | Arg |
| | | 185 | | | | | 190 | | | | 195 |
| Ala | Tyr | Ala | Asp | Met | Ala | Tyr | Pro | | | | |
| | | 200 | | | | | | | | | |

( 2 ) INFORMATION FOR SEQ ID NO:5:

( i ) SEQUENCE CHARACTERISTICS:
        ( A ) LENGTH: 323
        ( B ) TYPE: amino acid
        ( C ) STRANDEDNESS: single
        ( D ) TOPOLOGY: linear ( x i ) SEQUENCE DESCRIPTION: SEQ ID NO:5:

| Met | Ala | Ser | Met | Thr | Gly | Gly | Gln | Gln | Met | Gly | Arg | Gly | Ser |
|---|---|---|---|---|---|---|---|---|---|---|---|---|---|
| | | | | 5 | | | | | 10 | | | | |
| Gly | Ser | Met | Gly | His | His | His | His | His | His | His | His | | |
| 15 | | | | 20 | | | | | 25 | | | | |
| Ser | Ser | Gly | His | Ile | Glu | Gly | Arg | His | Met | Leu | Glu | Gly | Ser |
| 30 | | | | | 35 | | | | | 40 | | | |
| Pro | Ala | Asp | His | Ala | Arg | Glu | Ala | Arg | Ala | Val | Gly | Arg | Gly |
| | | 45 | | | | 50 | | | | | 55 | | |
| Pro | Ser | Ser | Ala | Ala | Pro | Ala | Ala | Pro | Gly | Arg | Thr | Pro | Pro |
| | | | 60 | | | | 65 | | | | | | 70 |
| Pro | Pro | Gly | Pro | Pro | Pro | Leu | Ser | Glu | Ala | Ala | Pro | Lys | Pro |
| | | | | 75 | | | | 80 | | | | | |
| Arg | Ala | Ala | Ala | Arg | Thr | Pro | Ala | Ala | Ser | Ala | Gly | Arg | Ile |
| 85 | | | | | 90 | | | | | 95 | | | |
| Glu | Arg | Arg | Arg | Ala | Arg | Ala | Ala | Val | Ala | Gly | Arg | Asp | Ala |
| | 100 | | | | | 105 | | | | | 110 | | |
| Thr | Gly | Arg | Phe | Thr | Ala | Gly | Gln | Pro | Arg | Arg | Val | Glu | Leu |
| | | | 115 | | | | 120 | | | | | 125 | |
| Asp | Ala | Asp | Ala | Thr | Ser | Gly | Ala | Phe | Tyr | Ala | Arg | Tyr | Arg |
| | | | 130 | | | | | 135 | | | | | 140 |
| Asp | Gly | Tyr | Val | Ser | Gly | Glu | Pro | Trp | Pro | Gly | Ala | Gly | Pro |
| | | | | 145 | | | | 150 | | | | | |
| Pro | Pro | Pro | Gly | Arg | Val | Leu | Tyr | Gly | Gly | Leu | Gly | Asp | Ser |
| 155 | | | | | 160 | | | | 165 | | | | |
| Arg | Pro | Gly | Leu | Trp | Gly | Ala | Pro | Glu | Ala | Glu | Glu | Ala | Arg |
| | 170 | | | | | 175 | | | | | 180 | | |
| Arg | Arg | Phe | Glu | Ala | Ser | Gly | Ala | Pro | Ala | Ala | Val | Trp | Ala |
| | | 185 | | | | | 190 | | | | | 195 | |
| Pro | Glu | Leu | Gly | Asp | Ala | Ala | Gln | Gln | Tyr | Ala | Leu | Ile | Thr |
| | | | | 200 | | | | | 205 | | | | 210 |
| Arg | Leu | Leu | Tyr | Thr | Pro | Asp | Ala | Glu | Ala | Met | Gly | Trp | Leu |
| | | | | 215 | | | | | 220 | | | | |
| Gln | Asn | Pro | Arg | Val | Val | Pro | Gly | Asp | Val | Ala | Leu | Asp | Gln |
| 225 | | | | | 230 | | | | | 235 | | | |
| Ala | Cys | Phe | Arg | Ile | Ser | Gly | Ala | Ala | Arg | Asn | Ser | Ser | Ser |
| | | 240 | | | | | 245 | | | | | 250 | |
| Phe | Ile | Tyr | Gly | Ser | Val | Ala | Arg | Ala | Val | Pro | His | Leu | Gln |
| | | | 255 | | | | | 260 | | | | | 265 |
| Tyr | Ala | Met | Ala | Ala | Glu | Arg | Phe | Gly | Trp | Gly | Leu | Ala | His |

|  | 270 |  |  |  |  | 275 |  |  |  |  | 280 |  |
|---|---|---|---|---|---|---|---|---|---|---|---|---|
| Ala | Ala | Ala | Ala | Val | Ala | Met | Ser | Arg | Arg | Tyr | Asp | Arg | Ala |
|  |  |  |  | 285 |  |  |  |  | 290 |  |  |  |

Gln Lys Gly Phe Leu Leu Thr Ser Leu Arg Arg Ala Tyr Ala
295              300                305

Pro Leu Leu Ala Arg Glu Asn Ala Ala Leu Thr Gly Ala Ala
    310              315                320

Gly ( 2 ) INFORMATION FOR SEQ ID NO:6:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGGAGGACAG TGCGGNNNNN NNNNNNNNNN NNNNNNNNNN NNNNNNNNNN      50

NNNNNCAGTG CGTCAGTCAA C      71

( 2 ) INFORMATION FOR SEQ ID NO:7:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGGAGGACAG TGCGG      15

( 2 ) INFORMATION FOR SEQ ID NO:8:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i x ) FEATURE:
        ( D ) OTHER INFORMATION: N is biotin ( x i ) SEQUENCE DESCRIPTION: SEQ ID NO:8:

NNNGTTGACT GACGCACTG      19

( 2 ) INFORMATION FOR SEQ ID NO:9:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO:9:

ACCAAGCTTG GGAGGACAGT GCGG      24

( 2 ) INFORMATION FOR SEQ ID NO:10:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGCGGATCCG TTGACTGACG CACTG                                                        25

( 2 ) INFORMATION FOR SEQ ID NO:11:

( i ) SEQUENCE CHARACTERISTICS:
        ( A ) LENGTH: 104
        ( B ) TYPE: nucleic acid
        ( C ) STRANDEDNESS: single
        ( D ) TOPOLOGY: linear ( x i ) SEQUENCE DESCRIPTION: SEQ ID NO:11:

TAATACGACT CACTATAGGG AGACAAGAAT AAACGCTCAA NNNNNNNNNN                              50

NNNNNNNNNN NNNNNNNNNN NNNNNNNNNN TTCGACAGGA GGCTCACAAC                              100

AGGC                                                                               104

( 2 ) INFORMATION FOR SEQ ID NO:12:

( i ) SEQUENCE CHARACTERISTICS:
        ( A ) LENGTH: 87
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGGAGACAAG AAUAAACGCU CAANNNNNNN NNNNNNNNNN NNNNNNNNNN                              50

NNNNNNNNNN NNNUUCGACA GGAGGCUCAC AACAGGC                                            87

( 2 ) INFORMATION FOR SEQ ID NO:13:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO:13:

TAATACGACT CACTATAGGG AGACAA                                                       26

( 2 ) INFORMATION FOR SEQ ID NO:14:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO:14:

GCCTGTTGTG AGCCTCCTGT CGAA                                                         24

( 2 ) INFORMATION FOR SEQ ID NO:15:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( x i ) SEQUENCE DESCRIPTION: SEQ ID NO:15:

CAGAAGCTTA ATACGACTCA CTATAGGGAG ACAAGAATAA ACGCTCAA                               48

( 2 ) INFORMATION FOR SEQ ID NO:16:

( i ) SEQUENCE CHARACTERISTICS:
        ( A ) LENGTH: 34
        ( B ) TYPE: nucleic acid (C) STRANDEDNESS: single
(D) TOPOLOGY: linear (x i) SEQUENCE DESCRIPTION: SEQ ID NO:16:

GACTGGATCC GCCTGTTGTG AGCCTCCTGT CGAA    34

(2) INFORMATION FOR SEQ ID NO:17:

(i) SEQUENCE CHARACTERISTICS:
      (A) LENGTH: 71
      (B) TYPE: nucleic acid
      (C) STRANDEDNESS: single
      (D) TOPOLOGY: linear (x i) SEQUENCE DESCRIPTION: SEQ ID NO:17:

GGGAGGACAG TGCGGCCCTT ATACGATTTT CGCGCATATC GTATCCCGCC    50

GCCTTCAGTG CGTCAGTCAA C    71

(2) INFORMATION FOR SEQ ID NO:18:

(i) SEQUENCE CHARACTERISTICS:
      (A) LENGTH: 71
      (B) TYPE: nucleic acid
      (C) STRANDEDNESS: single
      (D) TOPOLOGY: linear (x i) SEQUENCE DESCRIPTION: SEQ ID NO:18:

GGGAGGACAG TGCGGCCCAT GATTTTCTT TGACGATTTT CACGTATATC    50

GTCTCCAGTG CGTCAGTCAA C    71

(2) INFORMATION FOR SEQ ID NO:19:

(i) SEQUENCE CHARACTERISTICS:
      (A) LENGTH: 71
      (B) TYPE: nucleic acid
      (C) STRANDEDNESS: single
      (D) TOPOLOGY: linear (x i) SEQUENCE DESCRIPTION: SEQ ID NO:19:

GGGAGGACAG TGCGGCCACT CACGATTTTC GCGTATATCG TCCCTCCTGC    50

TTTTGCAGTG CGTCAGTCAA C    71

(2) INFORMATION FOR SEQ ID NO:20:

(i) SEQUENCE CHARACTERISTICS:
      (A) LENGTH: 70
      (B) TYPE: nucleic acid
      (C) STRANDEDNESS: single
      (D) TOPOLOGY: linear (x i) SEQUENCE DESCRIPTION: SEQ ID NO:20:

GGGAGGACAG TGCGGCCATG TTTCTTATCG TGACGATTTT CGCGTATATC    50

GTCGCAGTGC GTCAGTCAAC    70

(2) INFORMATION FOR SEQ ID NO:21:

(i) SEQUENCE CHARACTERISTICS:
      (A) LENGTH: 71
      (B) TYPE: nucleic acid
      (C) STRANDEDNESS: single
      (D) TOPOLOGY: linear (x i) SEQUENCE DESCRIPTION: SEQ ID NO:21:

GGGAGGACAG TGCGGTCTCC CGTACGATTT TCACGCATAT CGTACCCTGC    50

TGCTGCAGTG CGTCAGTCAA C                                                      71

( 2 ) INFORMATION FOR SEQ ID NO:22:

( i ) SEQUENCE CHARACTERISTICS:
          ( A ) LENGTH: 71
          ( B ) TYPE: nucleic acid
          ( C ) STRANDEDNESS: single
          ( D ) TOPOLOGY: linear ( x i ) SEQUENCE DESCRIPTION: SEQ ID NO:22:

GGGAGGACAG TGCGGCCCAG ATGGGTGTCA TACGATTTTC ACGTATATCG                        50

TATTTCAGTG CGTCAGTCAA C                                                      71

( 2 ) INFORMATION FOR SEQ ID NO:23:

( i ) SEQUENCE CHARACTERISTICS:
          ( A ) LENGTH: 71
          ( B ) TYPE: nucleic acid
          ( C ) STRANDEDNESS: single
          ( D ) TOPOLOGY: linear ( x i ) SEQUENCE DESCRIPTION: SEQ ID NO:23:

GGGAGGACAG TGCGGCCCGG CGATTTTCAC GTATATCGCC CACCTGTTGA                        50

GTCTTCAGTG CGTCAGTCAA C                                                      71

( 2 ) INFORMATION FOR SEQ ID NO:24:

( i ) SEQUENCE CHARACTERISTICS:
          ( A ) LENGTH: 71
          ( B ) TYPE: nucleic acid
          ( C ) STRANDEDNESS: single
          ( D ) TOPOLOGY: linear ( x i ) SEQUENCE DESCRIPTION: SEQ ID NO:24:

GGGAGGACAG TGCGGCGCCT ACATGTGCGA ACGATTTTCA CGCATATCGT                        50

TTTGCCAGTG CGTCAGTCAA C                                                      71

( 2 ) INFORMATION FOR SEQ ID NO:25:

( i ) SEQUENCE CHARACTERISTICS:
          ( A ) LENGTH: 71
          ( B ) TYPE: nucleic acid
          ( C ) STRANDEDNESS: single
          ( D ) TOPOLOGY: linear ( x i ) SEQUENCE DESCRIPTION: SEQ ID NO:25:

GGGAGGACAG TGCGGCCAAT GCCACTCTGA TAACGATTTT CACGTATATC                        50

GGTGTCAGTG CGTCAGTCAA C                                                      71

( 2 ) INFORMATION FOR SEQ ID NO:26:

( i ) SEQUENCE CHARACTERISTICS:
          ( A ) LENGTH: 71
          ( B ) TYPE: nucleic acid
          ( C ) STRANDEDNESS: single
          ( D ) TOPOLOGY: linear ( x i ) SEQUENCE DESCRIPTION: SEQ ID NO:26:

GGGAGGACAG TGCGGGGCAA CCGTAAACTA CGATTTTCGC GTATATCGTA                        50

GTATGCAGTG CGTCAGTCAA C                                                      71

( 2 ) INFORMATION FOR SEQ ID NO:27:

( i ) SEQUENCE CHARACTERISTICS:
( A ) LENGTH: 74
( B ) TYPE: nucleic acid
( C ) STRANDEDNESS: single
( D ) TOPOLOGY: linear ( x i ) SEQUENCE DESCRIPTION: SEQ ID NO:27:

GGGAGGACAG TGCGGCGGCC CACTTCGTTC CCCCGACGAT TTTCGCGTAT         50

ATCGTCGCCA GTGCGTCAGT CAAC         74

( 2 ) INFORMATION FOR SEQ ID NO:28:

( i ) SEQUENCE CHARACTERISTICS:
( A ) LENGTH: 71
( B ) TYPE: nucleic acid
( C ) STRANDEDNESS: single
( D ) TOPOLOGY: linear ( x i ) SEQUENCE DESCRIPTION: SEQ ID NO:28:

GGGAGGACAG TGCGGCGCCT ACACCACGAT TTTCACGCAT ATCGTGGTAC         50

CTTTTCAGTG CGTCAGTCAA C         71

( 2 ) INFORMATION FOR SEQ ID NO:29:

( i ) SEQUENCE CHARACTERISTICS:
( A ) LENGTH: 69
( B ) TYPE: nucleic acid
( C ) STRANDEDNESS: single
( D ) TOPOLOGY: linear ( x i ) SEQUENCE DESCRIPTION: SEQ ID NO:29:

GGGAGGACAG TGCGGCCAGA TATTAAACGA TTTCACGCAT ATCGTTTAGT         50

ACACAGTGCG TCAGTCAAC         69

( 2 ) INFORMATION FOR SEQ ID NO:30:

( i ) SEQUENCE CHARACTERISTICS:
( A ) LENGTH: 75
( B ) TYPE: nucleic acid
( C ) STRANDEDNESS: single
( D ) TOPOLOGY: linear ( x i ) SEQUENCE DESCRIPTION: SEQ ID NO:30:

GGGAGGACAG TGCGGCCACA TCACGCAGAC GACCGTCATT TTCACGCATA         50

TCGTCCCTTC AGTGCGTCAG TCAAC         75

( 2 ) INFORMATION FOR SEQ ID NO:31:

( i ) SEQUENCE CHARACTERISTICS:
( A ) LENGTH: 71
( B ) TYPE: nucleic acid
( C ) STRANDEDNESS: single
( D ) TOPOLOGY: linear ( x i ) SEQUENCE DESCRIPTION: SEQ ID NO:31:

GGGAGGACAG TGCGGCCCTG CTGTTTCCGT GATCGTCAGG TAAGACCGAT         50

CGTCACAGTG CGTCAGTCAA C         71

( 2 ) INFORMATION FOR SEQ ID NO:32:

( i ) SEQUENCE CHARACTERISTICS:
( A ) LENGTH: 71
( B ) TYPE: nucleic acid
( C ) STRANDEDNESS: single
( D ) TOPOLOGY: linear ( x i ) SEQUENCE DESCRIPTION: SEQ ID NO:32:

GGGAGGACAG TGCGGCTGGA TCGTATGGCA ATATGATCCC CCACCCCATC 50

CGTCTCAGTG CGTCAGTCAA C 71

( 2 ) INFORMATION FOR SEQ ID NO:33:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:33:

GGGAGGACAG TGCGGTCACG TGTACCATCG TCTGGGAATA CGATGCTTTT 50

TTGTCCAGTG CGTCAGTCAA C 71

( 2 ) INFORMATION FOR SEQ ID NO:34:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGGAGGACAG TGCGGCACAA GACCTCGATC GTATGGTAAT ATCGATCTCC 50

TTCGACAGTG CGTCAGTCAA C 71

( 2 ) INFORMATION FOR SEQ ID NO:35:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:35:

GGGAGGACAG TGCGGTCCCG CGGCGCATCG TCTGGCAATA CGATGTCATG 50

GCTTACAGTG CGTCAGTCAA C 71

( 2 ) INFORMATION FOR SEQ ID NO:36:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:36:

GGGAGGACAG TGCGGCCGGC TTACTATGTG ATCGTATGGG AATATGATCT 50

TATTGCAGTG CGTCAGTCAA C 71

( 2 ) INFORMATION FOR SEQ ID NO:37:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGGAGGACAG TGCGGCACGA ACTTTCATCG TATGGGAATA TGATGTTTTT 50

CTTTCAGTGC GTCAGTCAAC                                                        70

(2) INFORMATION FOR SEQ ID NO:38:

(i) SEQUENCE CHARACTERISTICS:
        (A) LENGTH: 71
        (B) TYPE: nucleic acid
        (C) STRANDEDNESS: single
        (D) TOPOLOGY: linear (xi) SEQUENCE DESCRIPTION: SEQ ID NO:38:

GGGAGGACAG TGCGGCCATC TCAGATCGTA TGGTAATATT GATCTTCTTG                        50

CACCTCAGTG CGTCAGTCAA C                                                      71

(2) INFORMATION FOR SEQ ID NO:39:

(i) SEQUENCE CHARACTERISTICS:
        (A) LENGTH: 71
        (B) TYPE: nucleic acid
        (C) STRANDEDNESS: single
        (D) TOPOLOGY: linear (xi) SEQUENCE DESCRIPTION: SEQ ID NO:39:

GGGAGGACAG TGCGGCCACA CCCACCCATC GCCTGGTAAT GCGATGTTCC                        50

CGGACCAGTG CGTCAGTCAA C                                                      71

(2) INFORMATION FOR SEQ ID NO:40:

(i) SEQUENCE CHARACTERISTICS:
        (A) LENGTH: 71
        (B) TYPE: nucleic acid
        (C) STRANDEDNESS: single
        (D) TOPOLOGY: linear (xi) SEQUENCE DESCRIPTION: SEQ ID NO:40:

GGGAGGACAG TGCGGCCCCA CGCAATATCG CATGGTAATG CCGATTACTA                        50

CCATGCAGTG CGTCAGTCAA C                                                      71

(2) INFORMATION FOR SEQ ID NO:41:

(i) SEQUENCE CHARACTERISTICS:
        (A) LENGTH: 71
        (B) TYPE: nucleic acid
        (C) STRANDEDNESS: single
        (D) TOPOLOGY: linear (xi) SEQUENCE DESCRIPTION: SEQ ID NO:41:

GGGAGGACAG TGCGGTGCCC TGAATCGCTT GGTAATGCGA CGCAGCCATT                        50

ATGGTCAGTG CGTCAGTCAA C                                                      71

(2) INFORMATION FOR SEQ ID NO:42:

(i) SEQUENCE CHARACTERISTICS:
        (A) LENGTH: 70
        (B) TYPE: nucleic acid
        (C) STRANDEDNESS: single
        (D) TOPOLOGY: linear (xi) SEQUENCE DESCRIPTION: SEQ ID NO:42:

GGGAGGACAG TGCGGCGTGA CGTATGGTAT GGTAATACCG ATCTTGTCCC                        50

GCAACAGTGC GTCAGTCAAC                                                        70

(2) INFORMATION FOR SEQ ID NO:43:

( i ) SEQUENCE CHARACTERISTICS:
  ( A ) LENGTH: 71
  ( B ) TYPE: nucleic acid
  ( C ) STRANDEDNESS: single
  ( D ) TOPOLOGY: linear ( x i ) SEQUENCE DESCRIPTION: SEQ ID NO:43:

GGGAGGACAG TGCGGCCCTT TACGATCGCA TGGTAATGCT GATCCTATAT  50

TCCCCCAGTG CGTCAGTCAA C  71

( 2 ) INFORMATION FOR SEQ ID NO:44:

( i ) SEQUENCE CHARACTERISTICS:
    ( A ) LENGTH: 69
    ( B ) TYPE: nucleic acid
    ( C ) STRANDEDNESS: single
    ( D ) TOPOLOGY: linear ( x i ) SEQUENCE DESCRIPTION: SEQ ID NO:44:

GGGAGGACAG TGCGGCGTGA CGTATCTATG GTAATACCGA TCTTATCCCG  50

CAACAGTGCG TCAGTCAAC  69

( 2 ) INFORMATION FOR SEQ ID NO:45:

( i ) SEQUENCE CHARACTERISTICS:
    ( A ) LENGTH: 70
    ( B ) TYPE: nucleic acid
    ( C ) STRANDEDNESS: single
    ( D ) TOPOLOGY: linear ( x i ) SEQUENCE DESCRIPTION: SEQ ID NO:45:

GGGAGGACAG TGCGGGGGGA TCGTCTGGTA ATACGATACC TGTTTTTCAA  50

TGCTCAGTGC GTCAGTCAAC  70

( 2 ) INFORMATION FOR SEQ ID NO:46:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( x i ) SEQUENCE DESCRIPTION: SEQ ID NO:46:

GGGAGGACAG TGCGGGGGGC TGGTGAGCAC ATCGTATGGC AATACGATGC  50

TTATACAGTG CGTCAGTCAA C  71

( 2 ) INFORMATION FOR SEQ ID NO:47:

( i ) SEQUENCE CHARACTERISTICS:
    ( A ) LENGTH: 74
    ( B ) TYPE: nucleic acid
    ( C ) STRANDEDNESS: single
    ( D ) TOPOLOGY: linear ( x i ) SEQUENCE DESCRIPTION: SEQ ID NO:47:

GGGAGGACAG TGCGGCGGCC GGCTACCTGC TGATATCGTA TGGTAATATG  50

ATTGTACACA GTGCGTCAGT CAAC  74

( 2 ) INFORMATION FOR SEQ ID NO:48:

( i ) SEQUENCE CHARACTERISTICS:
    ( A ) LENGTH: 75
    ( B ) TYPE: nucleic acid
    ( C ) STRANDEDNESS: single
    ( D ) TOPOLOGY: linear ( x i ) SEQUENCE DESCRIPTION: SEQ ID NO:48:

GGGAGGACAG TGCGGCGGCC TTAGTGATCG TCTGGTAATA CGATCCTCTT        50

TGCTGCACGC AGTGCGTCAG TCAAC        75

( 2 ) INFORMATION FOR SEQ ID NO:49:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:49:

GGGAGGACAG TGCGGCACAG GCATCGTATG GGAATACCGA TGCTTCCGTA        50

ATTCACAGTG CGTCAGTCAA C        71

( 2 ) INFORMATION FOR SEQ ID NO:50:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:50:

GGGAGGACAG TGCGGCCACC ATGATCGTAT GGGAATATTG ATCTCCTGTC        50

GGCTACAGTG CGTCAGTCAA C        71

( 2 ) INFORMATION FOR SEQ ID NO:51:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGGAGGACAG TGCGGCCACC ATCGTATGGT AATACTGATG TTCCCATGTG        50

CGGGCAGTGC GTCAGTCAAC        70

( 2 ) INFORMATION FOR SEQ ID NO:52:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( x i ) SEQUENCE DESCRIPTION: SEQ ID NO:52:

GGGAGGACAG TGCGGCCCCT CGATCGTATG GGAATACCGA TCACGATTTT        50

CGCGCAGTGC GTCAGTCAAC        70

( 2 ) INFORMATION FOR SEQ ID NO:53:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( x i ) SEQUENCE DESCRIPTION: SEQ ID NO:53:

GGGAGGACAG TGCGGTAGGG TAAGTGGTGT GTAAATTCTA GCCCCATCAT        50

CTGTGCAGTG CGTCAGTCAA C        71

( 2 ) INFORMATION FOR SEQ ID NO:54:

( i ) SEQUENCE CHARACTERISTICS:
        ( A ) LENGTH: 66
        ( B ) TYPE: nucleic acid
        ( C ) STRANDEDNESS: single
        ( D ) TOPOLOGY: linear ( x i ) SEQUENCE DESCRIPTION: SEQ ID NO:54:

```
GGGAGGACAG TGCGGCTGTG GTTGAAGAAG TGGACGTCGT GGGATCGGGA          50
CAGTGCGTCA GTCAAC                                                66
```

( 2 ) INFORMATION FOR SEQ ID NO:55:

( i ) SEQUENCE CHARACTERISTICS:
        ( A ) LENGTH: 66
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
GGGAGGACAG TGCGGTGACA ATGTTGTCGG GGTTCGATGA CCATGTGTAT          50
CAGTGCGTCA GTCAAC                                                66
```

( 2 ) INFORMATION FOR SEQ ID NO:56:

( i ) SEQUENCE CHARACTERISTICS:
        ( A ) LENGTH: 65
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
GGGAGGACAG TGCGGGCAGG AGGTCAGCTG AGGTCGGAAG AGTGCTAGGC          50
AGTGCGTCAG TCAAC                                                 65
```

( 2 ) INFORMATION FOR SEQ ID NO:57:

( i ) SEQUENCE CHARACTERISTICS:
        ( A ) LENGTH: 66
        ( B ) TYPE: nucleic acid
        ( C ) STRANDEDNESS: single
        ( D ) TOPOLOGY: linear ( x i ) SEQUENCE DESCRIPTION: SEQ ID NO:57:

```
GGGAGGACAG TGCGGTCCTT GGTGTGGATA TGGGGGAACG GTTCGACCGA          50
CAGTGCGTCA GTCAAC                                                66
```

( 2 ) INFORMATION FOR SEQ ID NO:58:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( x i ) SEQUENCE DESCRIPTION: SEQ ID NO:58:

```
TTTCRCGYAT                                                       10
```

( 2 ) INFORMATION FOR SEQ ID NO:59:

( i ) SEQUENCE CHARACTERISTICS:
        ( A ) LENGTH: 36
        ( B ) TYPE: nucleic acid (C) STRANDEDNESS: single
(D) TOPOLOGY: linear (x i) SEQUENCE DESCRIPTION: SEQ ID NO:59:

CCCTTATACG ATTTTCGCGC ATATCGTATC CCGCCG    36

(2) INFORMATION FOR SEQ ID NO:60:

(i) SEQUENCE CHARACTERISTICS:
       (A) LENGTH: 28
       (B) TYPE: nucleic acid
       (C) STRANDEDNESS: single
       (D) TOPOLOGY: linear (x i) SEQUENCE DESCRIPTION: SEQ ID NO:60:

TTATACGATT TTCGCGCATA TCGTATCC    28

(2) INFORMATION FOR SEQ ID NO:61:

(i) SEQUENCE CHARACTERISTICS:
       (A) LENGTH: 24
       (B) TYPE: nucleic acid
       (C) STRANDEDNESS: single
       (D) TOPOLOGY: linear (x i) SEQUENCE DESCRIPTION: SEQ ID NO:61:

ATACGATTTT CGCGCATATC GTAT    24

(2) INFORMATION FOR SEQ ID NO:62:

(i) SEQUENCE CHARACTERISTICS:
       (A) LENGTH: 31
       (B) TYPE: nucleic acid
       (C) STRANDEDNESS: single
       (D) TOPOLOGY: linear (x i) SEQUENCE DESCRIPTION: SEQ ID NO:62:

CTCTGATAAC GATTTTCACG TATATCGGTG T    31

(2) INFORMATION FOR SEQ ID NO:63:

(i) SEQUENCE CHARACTERISTICS:
       (A) LENGTH: 33
       (B) TYPE: nucleic acid
       (C) STRANDEDNESS: single
       (D) TOPOLOGY: linear (x i) SEQUENCE DESCRIPTION: SEQ ID NO:63:

TACACCACGA TTTTCACGCA TATCGTGGTA CCT    33

(2) INFORMATION FOR SEQ ID NO:64:

(i) SEQUENCE CHARACTERISTICS:
       (A) LENGTH: 36
       (B) TYPE: nucleic acid
       (C) STRANDEDNESS: single
       (D) TOPOLOGY: linear (x i) SEQUENCE DESCRIPTION: SEQ ID NO:64:

CCCCACGCAA TATCGCATGG TAATGCCGAT TACTAC    36

(2) INFORMATION FOR SEQ ID NO:65:

(i) SEQUENCE CHARACTERISTICS:
       (A) LENGTH: 34
       (B) TYPE: nucleic acid
       (C) STRANDEDNESS: single
       (D) TOPOLOGY: linear ( x i ) SEQUENCE DESCRIPTION: SEQ ID NO:65:

CGTGACGTAT GGTATGGTAA TACCGATCTT GTCC     34

( 2 ) INFORMATION FOR SEQ ID NO:66:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO:66:

CCATCTCAGA TCGTATGGTA ATATTGATCT TCTTGC     36

( 2 ) INFORMATION FOR SEQ ID NO:67:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO:67:

GGGGATCGTC TGGTAATACG ATCCC     25

( 2 ) INFORMATION FOR SEQ ID NO:68:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO:68:

GGGCCCATAC GATTTTTTTT TTATCGTATG GGCCC     35

( 2 ) INFORMATION FOR SEQ ID NO:69:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO:69:

GGGCCCATAC GATTTCGCG CATATCGTAT GGGCCC     36

( 2 ) INFORMATION FOR SEQ ID NO:70:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO:70:

CCCTTATACG ACTGGTAATA TCGTATCCCG CCG     33

( 2 ) INFORMATION FOR SEQ ID NO:71:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO:71:

CCCTTATACG AGGTATCGTA TCCCGCCG     28

(2) INFORMATION FOR SEQ ID NO:72:

(i) SEQUENCE CHARACTERISTICS:
        (A) LENGTH: 27
        (B) TYPE: nucleic acid
        (C) STRANDEDNESS: single
        (D) TOPOLOGY: linear (xi) SEQUENCE DESCRIPTION: SEQ ID NO:72:

GGGGATCGTT TTCGCGCATA CGATCCC     27

(2) INFORMATION FOR SEQ ID NO:73:

(i) SEQUENCE CHARACTERISTICS:
        (A) LENGTH: 28
        (B) TYPE: nucleic acid
        (C) STRANDEDNESS: single
        (D) TOPOLOGY: linear (ix) FEATURE:
        (D) OTHER INFORMATION: N is C5- methyl-dC (xi) SEQUENCE DESCRIPTION: SEQ ID NO:73:

TTATANGATT TTCGCGCATA TNGTATCC     28

(2) INFORMATION FOR SEQ ID NO:74:

(i) SEQUENCE CHARACTERISTICS:
        (A) LENGTH: 36
        (B) TYPE: nucleic acid
        (C) STRANDEDNESS: single
        (D) TOPOLOGY: linear (ix) FEATURE:
        (D) OTHER INFORMATION: Nucleotides 1- 4 and
        32-36 are bonded by a phosphorothioate
        linkage (xi) SEQUENCE DESCRIPTION: SEQ ID NO:74:

TATATTATAC GATTTCGCG CATATCGTAT CCTATA     36

(2) INFORMATION FOR SEQ ID NO:75:

(i) SEQUENCE CHARACTERISTICS:
        (A) LENGTH: 87
        (B) TYPE: nucleic acid
        (C) STRANDEDNESS: single
        (D) TOPOLOGY: linear (xi) SEQUENCE DESCRIPTION: SEQ ID NO:75:

GGGAGACAAG AAUAAACGCU CAAAAGAACC AAAGGGAAGG GGGAAGAGGG     50

AAGAGGGAUG UGGUUCGACA GGAGGCUCAC AACAGGC     87

(2) INFORMATION FOR SEQ ID NO:76:

(i) SEQUENCE CHARACTERISTICS:
        (A) LENGTH: 87
        (B) TYPE: nucleic acid
        (C) STRANDEDNESS: single
        (D) TOPOLOGY: linear (xi) SEQUENCE DESCRIPTION: SEQ ID NO:76:

GGGAGACAAG AAUAAACGCU CAAAAGAACC AAAGGGAAGG GGGAAGAGGG     50

AAGCGGGAUG UGGUUCGACA GGAGGCUCAC AACAGGC     87

( 2 ) INFORMATION FOR SEQ ID NO:77:

( i ) SEQUENCE CHARACTERISTICS:
           ( A ) LENGTH: 87
           ( B ) TYPE: nucleic acid
           ( C ) STRANDEDNESS: single
           ( D ) TOPOLOGY: linear ( x i ) SEQUENCE DESCRIPTION: SEQ ID NO:77:

| | | | | | |
|---|---|---|---|---|---|
| GGGAGACAAG | AAUAAACGCU | CAAAAGAACC | AAAGGGAAGA | GGGAAGAGGG | 50 |
| AAGAGGGAUG | UGGUUCGACA | GGAGGCUCAC | AACAGGC | | 87 |

( 2 ) INFORMATION FOR SEQ ID NO:78:

( i ) SEQUENCE CHARACTERISTICS:
           ( A ) LENGTH: 87
           ( B ) TYPE: nucleic acid
           ( C ) STRANDEDNESS: single
           ( D ) TOPOLOGY: linear ( x i ) SEQUENCE DESCRIPTION: SEQ ID NO:78:

| | | | | | |
|---|---|---|---|---|---|
| GGGAGACAAG | AAUAAACGCU | CAAAAGAACC | AAAGGGAAGG | GGGAAGAGGG | 50 |
| AAGAGGGAUG | UGGUUCGACA | GGAGGCUCAC | AACAGGC | | 87 |

( 2 ) INFORMATION FOR SEQ ID NO:79:

( i ) SEQUENCE CHARACTERISTICS:
           ( A ) LENGTH: 87
           ( B ) TYPE: nucleic acid
           ( C ) STRANDEDNESS: single
           ( D ) TOPOLOGY: linear ( x i ) SEQUENCE DESCRIPTION: SEQ ID NO:79:

| | | | | | |
|---|---|---|---|---|---|
| GGGAGACAAG | AAUAAACGCU | CAAAAGAACC | AAUGGGAAGA | GGGAAGAGGU | 50 |
| AAGAGGGAUG | UGGUUCGACA | GGAGGCUCAC | AACAGGC | | 87 |

( 2 ) INFORMATION FOR SEQ ID NO:80:

( i ) SEQUENCE CHARACTERISTICS:
           ( A ) LENGTH: 87
           ( B ) TYPE: nucleic acid
           ( C ) STRANDEDNESS: single
           ( D ) TOPOLOGY: linear ( x i ) SEQUENCE DESCRIPTION: SEQ ID NO:80:

| | | | | | |
|---|---|---|---|---|---|
| GGGAGACAAG | AAUAAACGCU | CAAAGGAACC | AAAGGGAAGA | GGGAAGAGGG | 50 |
| ACGAGGGAUG | UGGUUCGACA | GGAGGCUCAC | AACAGGC | | 87 |

( 2 ) INFORMATION FOR SEQ ID NO:81:

( i ) SEQUENCE CHARACTERISTICS:
           ( A ) LENGTH: 87
           ( B ) TYPE: nucleic acid
           ( C ) STRANDEDNESS: single
           ( D ) TOPOLOGY: linear ( x i ) SEQUENCE DESCRIPTION: SEQ ID NO:81:

| | | | | | |
|---|---|---|---|---|---|
| GGGAGACAAG | AAUAAACGCU | CAAAAGAACC | AAAGGGAAGA | GGGAAGAGGG | 50 |
| AAGCGGGAUG | AGGUUCGACA | GGAGGCUCAC | AACAGGC | | 87 |

( 2 ) INFORMATION FOR SEQ ID NO:82:

( i ) SEQUENCE CHARACTERISTICS:
           ( A ) LENGTH: 87

(B) TYPE: nucleic acid
(C) STRANDEDNESS: single
(D) TOPOLOGY: linear (xi) SEQUENCE DESCRIPTION: SEQ ID NO:82:

GGGAGACAAG AAUAAACGCU CAAAAGAACC AAAGGGAAGG GGGAAGAGGG  50
AAGAGGGAUG AGGUUCGACA GGAGGCUCAC AACAGGC  87

(2) INFORMATION FOR SEQ ID NO:83:

(i) SEQUENCE CHARACTERISTICS:
(A) LENGTH: 87
(B) TYPE: nucleic acid
(C) STRANDEDNESS: single
(D) TOPOLOGY: linear (xi) SEQUENCE DESCRIPTION: SEQ ID NO:83:

GGGAGACAAG AAUAAACGCU CAAAGGAACC AAAGGGAAGG GGGAAGAGGG  50
AAGAGGGAUG UGGUUCGACA GGAGGCUCAC AACAGGC  87

(2) INFORMATION FOR SEQ ID NO:84:

(i) SEQUENCE CHARACTERISTICS:
(A) LENGTH: 87
(B) TYPE: nucleic acid
(C) STRANDEDNESS: single
(D) TOPOLOGY: linear (xi) SEQUENCE DESCRIPTION: SEQ ID NO:84:

GGGAGACAAG AAUAAACGCU CAAAAGAACC AAAGGGAAAA GGGAAGAGGG  50
AAGAGGGAUG UGGUUCGACA GGAGGCUCAC AACAGGC  87

(2) INFORMATION FOR SEQ ID NO:85:

(i) SEQUENCE CHARACTERISTICS:
(A) LENGTH: 87
(B) TYPE: nucleic acid
(C) STRANDEDNESS: single
(D) TOPOLOGY: linear (xi) SEQUENCE DESCRIPTION: SEQ ID NO:85:

GGGAGACAAG AAUAAACGCU CAAAAGAACC AAAGGGAAGA GGGAAGAGGG  50
AAGCGGGAUG UGGUUCGACA GGAGGCUCAC AACAGGC  87

(2) INFORMATION FOR SEQ ID NO:86:

(i) SEQUENCE CHARACTERISTICS:
(A) LENGTH: 86
(B) TYPE: nucleic acid
(C) STRANDEDNESS: single
(D) TOPOLOGY: linear (xi) SEQUENCE DESCRIPTION: SEQ ID NO:86:

GGGAGACAAG AAUAAACGCU CAAAGAACCG AAGGGAAGAG GGAAGAGGGA  50
AGAGGGAUGA GGUUCGACAG GAGGCUCACA ACAGGC  86

(2) INFORMATION FOR SEQ ID NO:87:

(i) SEQUENCE CHARACTERISTICS:
(A) LENGTH: 35
(B) TYPE: nucleic acid ( C ) STRANDEDNESS: single
( D ) TOPOLOGY: linear ( x i ) SEQUENCE DESCRIPTION: SEQ ID NO:87:

CCATTGGGGG AATCGTCACT GCCGCCCCTT TGGGG   35